US012644871B2

(12) United States Patent
Heller et al.

(10) Patent No.: US 12,644,871 B2

(45) Date of Patent: Jun. 2, 2026

(54) DETECTION OF NITRATES AND THEIR DECOMPOSITION PRODUCTS BY MEANS OF FLUORESCENCE MEASUREMENT

(71) Applicants: Bundesrepublik Deutschland, vertreten durch den Bundesminister für Wirtschaftund Energie, Berlin (DE); Institut Dr. Foerster GmbH & Co. KG, Reutlingen (DE)

(72) Inventors: Benedikt Heller, Berlin (DE); Mustafa Biyikal, Berlin (DE); Knut Rurack, Berlin (DE); Jerie Zbynek, Reutlingen (DE)

(73) Assignee: Bunderspublik Deutschland, vetreten durch den Bundesminister für Wirtschaft und Energie, Berlin (DE)

( * ) Notice: Subject to any disclaimer, the term of this patent is extended or adjusted under 35 U.S.C. 154(b) by 1172 days.

(21) Appl. No.: 17/616,636

(22) PCT Filed: Jun. 5, 2019

(86) PCT No.: PCT/EP2019/064697

§ 371 (c)(1),
(2) Date: Dec. 3, 2021

(87) PCT Pub. No.: WO2020/244755

PCT Pub. Date: Dec. 10, 2020

(65) Prior Publication Data

US 2022/0236243 A1 Jul. 28, 2022

(51) Int. Cl.

*C07F 5/02* (2006.01)
*G01N 21/77* (2006.01)
*G01N 31/22* (2006.01)
*G01N 33/00* (2006.01)

(52) U.S. Cl.

CPC ........... *G01N 31/227* (2013.01); *C07F 5/022* (2013.01); *C07F 5/027* (2013.01); *G01N 21/77* (2013.01); *G01N 33/0057* (2013.01); *G01N 2021/7786* (2013.01)

(58) Field of Classification Search

CPC ...... C07F 5/027; G01N 31/227; G01N 21/77; G01N 33/0057; G01N 2021/7786

See application file for complete search history.

(56) References Cited

U.S. PATENT DOCUMENTS

2015/0291628 A1 10/2015 Danaboyina et al.
2018/0372704 A1* 12/2018 Biyikal .............. G01N 33/0037
2020/0056994 A1* 2/2020 Rurack .............. G01N 33/0057

FOREIGN PATENT DOCUMENTS

WO 2017085137 A1 5/2017

OTHER PUBLICATIONS

Dilek, O. et al. "Synthesis of boron dipyrromethene fluorescent probes for bioorthogonal labeling," Tetrahedron Letters 49 (2008) 1413-1416 (Year: 2008).*

Yamaguchi, S. et al. "Tridurylboranes Extended by Three Arylethynyl Groups as a New Family of Boron-Based π-Electron Systems," Org. Lett., vol. 2, No. 26, 2000 (Year: 2000).*

Kubo, Y. et al. "A Colorimetric and Ratiometric Fluorescent Chemosensor with Three Emission Changes: Fluoride Ion Sensing by a Triarylborane-Porphyrin Conjugate," Angew. Chem. Int. Ed. 2003, 42, 2036-2040 (Year: 2003).*

Office Action dated Nov. 16, 2022 for corresponding Canadian application 3,142,537.

(Continued)

*Primary Examiner* — Jennifer Wecker

*Assistant Examiner* — Michelle Adams

(74) *Attorney, Agent, or Firm* — Bachman & LaPointe, P.C.

(57) ABSTRACT

A molecular probe for selective detection of a nitrate and/or a decomposition product of a nitrate by generating a fluorescence signal in response to an excitation in the wavelength range between 340-370 and 480-520 nm, wherein the molecular probe is selected from a triarylborane dye according to formula (7) and a BODIPY™ (boron-dipyrromethene) dye according to formula (13):

(7)

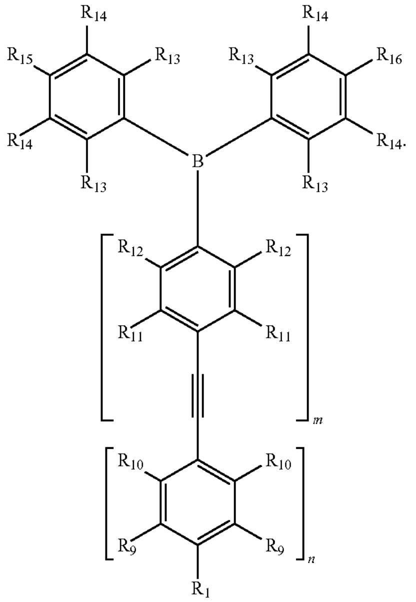

18 Claims, 15 Drawing Sheets

(56) References Cited

OTHER PUBLICATIONS

Mcquade et al., "Fluorescent probes to investigate nitric oxide and other reactive nitrogen species in biology (truncated form: fluorescent probes of reactive nitrogen species)", A Current Opinion in Chemical Biology, Current Biology Ltd, London, GB, vol. 14, No. 1, (Feb. 1, 2010), pp. 43-49, XP02689560.
Kolemen et al., "Reaction-based Bodipy probes for selective bio-imaging", Coordination Chemistry Reviews, vol. 354, (Jul. 17, 2017), pp. 121-134, XP085264739.
International search report for patent application No. PCT/EP2019/064697 dated Feb. 7, 2020.

* cited by examiner

DETECTION OF NITRATES AND THEIR DECOMPOSITION PRODUCTS BY MEANS OF FLUORESCENCE MEASUREMENT

FIELD AND BACKGROUND

The present invention relates to fluorescent molecular probes and fluorescence and products of their decomposition. The selective and sensitive detection of these analytes with the suggested sensor comprising the fluorescent molecular probe can help to prevent fatalities.

BRIEF SUMMARY

A sensor comprising an analyte sensitive layer for the selective detection of nitrate-based explosives e.g. ammonium nitrate, urea nitrate and furthermore nitric acid, nitrous acid and nitric oxides in solid or gas form is suggested. With respect to the area of application, the explosives exist in solid form and have to be detected as such, preferably after wipe sampling with a swab. For their chemical detection in the sensing device or instrument, however, the explosives have to be transferred into the gas phase, e.g. by heating the swab, guided to the analyte-responsive layer and be detected therein. Detection of e.g. NOx exhaust gases of a combustion engine or other anthropogenic emissions is not wanted. The analyte sensitive layer comprises a molecular probe selected from an organoborane dye, such as a triarylborane dye or a BODIPY™ dye (i.e. a boron difluoride group BF joined to a dipyrromethene group), that carries a reaction site consisting of at least one secondary and one secondary or primary amine, and a hydrophilic or hydrophobic carrier. Furthermore, a method for preparing same and a method for detecting an analyte, selected from nitrate-based explosives e.g. ammonium nitrate, urea nitrate and furthermore nitric acid, nitrous acid and nitric oxides, is suggested.

DETAILED DESCRIPTION OF THE INVENTION

Figure 1:
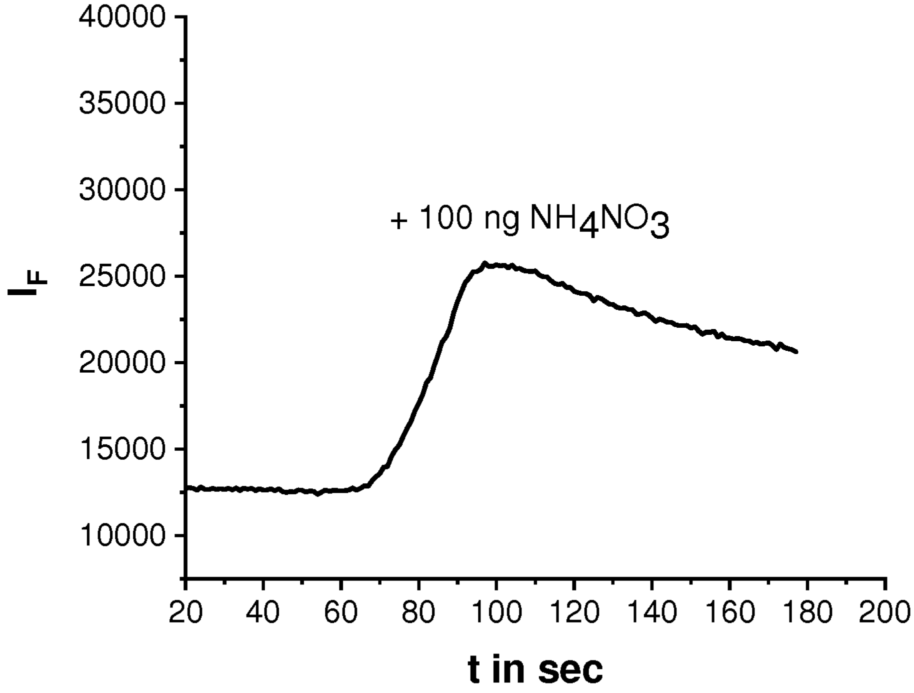
FIG. 1 shows the fluorescence intensity of the sensor of example 1 (the catalyst Nafion is drop-coated in the channel right before the sensor layer).

According to an embodiment the fluorescent indicator for a selective detection of an analyte selected from a nitrate-based substance, e.g. nitrate-based explosives such as e.g. ammonium nitrate, urea nitrate; and furthermore nitric acid, nitrous acid and nitric oxides comprises the following constituents:

- a molecular probe,
- a hydrophilic or a hydrophobic carrier material,
- a substrate;
- wherein the molecular probe and the carrier material are homogeneously distributed within an indicator layer which is deposited on the substrate; and wherein the molecular probe is selected from a triarylborane dye and a BODIPY™ dye. Herein the term "molecular probe" is considered as being synonymous to the terms "molecular sensor", "molecular indicator" and "molecular reporter".

Advantageously, the target analyte e.g. ammonium nitrate is decomposed to nitric acid respectively to nitric oxides thermally or upon contact with a sulfonic acid which acts as a catalyst. Thus, at and within the analyte sensitive layer the (decomposition products of the) analyte reacts/react with the triarylborane dye or with the BODIPY™ dye and the reaction products are optically detected by their specific fluorescence.

The corresponding reactions: catalytic decay and reaction with the indicator dyes take place at and within the carrier material (e.g. a polyurethane/polyether-based hydrogel such as Hydrogel D1 from AdvanSource Biomaterials Corp.) or within the carrier material polystyrene in a mixture of an organic solvent with water or in pure organic solvents which is/are applied to the substrate, e.g. by pipetting, spotting/coating.

The decomposition of the analyte(s) can additionally to or independently from the thermal decomposition also be initiated upon contact with a sulfonic acid. The sulfonic acid functions as a catalyst. The contact of the analyte(s) with the sulfonic acid can take place either directly within the chip before impinging on the sensor layer or with a wipe sample coated with the sulfonic acid.

Preferably, a mixture of the molecular probe with the carrier material and optionally the sulfonic acid and a solvent are deposited on the substrate with a (n) (automated) Nordson EFD dispenser/spotter. Typically, the analyte sensitive layer is thus fixed to the substrate, e.g. a glass or an optically transparent polymer foil and thermally stable at elevated temperatures, e.g. up to 150° C., preferably up to 175° C.

Alternatively, the sulfonic acid may be arranged separately from the indicator layer. Advantageously, it may be arranged on a swab or forming a swab or wipe which is used to swab/wipe a surface which might carry traces of the analyte. The swabbed/wiped surface might have been in contact with the analyte and still comprise minute quantities (traces) of it. Therefore, according to an embodiment, the swab/wipe may be used to collect a sample on such surfaces which is afterwards analyzed with an appropriate apparatus (e.g. "electronic nose") while or after being heated. Furthermore, the sulfonic acid, e.g. a foil or a tube comprising same, may be part of a sample collection device ("electronic nose"), said device comprising an inlet and an outlet, which is heated at least at its inlet opening up to 100° C., up to 150° C., or even up to 175° C. Advantageously, for such application, a perfluorosulfonic acid according to formula (5) may be used as a foil or separate layer.

According to an embodiment the sulfonic acid is selected from a substance according to formula (1), (2) and (3):

(1)

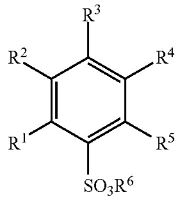

(2)

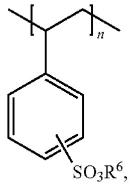

(3)

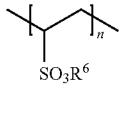

or their mixture, wherein $R^1$, $R^5$=H, Me, Et, Pr, alkyl, vinyl, phenyl, aryl, benzyl, F, Cl, Br, I, $CF_3$, $CH_2OH$, $CO_2H$, $PO_3H_2$, OH, OMe, O(alkyl), O(aryl), CN, $NO_2$, $NH_2$, $SO_3H$, or $SO_3$;

$R^2$, $R^4$=H, Me, Et, Pr, alkyl, vinyl, phenyl, aryl, benzyl, F, Cl, Br, I, $CF_3$, $CH_2OH$, $CO_2H$, $PO_3H_2$, OH, OMe, O(alkyl), O(aryl), CN, $NO_2$, $NH_2$, $SO_3H$, or $SO_3$;

$R^3$=H, Me, Et, Pr, alkyl, vinyl, phenyl, aryl, benzyl, F, Cl, Br, I, $CF_3$, $CH_2OH$, $CO_2H$, $PO_3H_2$, OH, OMe, O(alkyl), O(aryl), CN, $NO_2$, $NH_2$, $SO_3H$, or $SO_3$;

$R^6$=H, Na, K, Ag, tetrabutylammonium, or tetraoctylammonium;

or $R^1$, $R^2$, $R^3$, $R^4$, and $R^5$ are independently from each other =H, Me, Et, Pr, alkyl, vinyl, phenyl, aryl, benzyl, F, Cl, Br, I, $CF_3$, $CH_2OH$, $CO_2H$, $PO_3H_2$, OH, OMe, O(alkyl), O(aryl), CN, $NO_2$, $NH_2$, $SO_3H$, or $SO_3$;

$R^6$=H, Na, K, Ag, tetrabutylammonium, or tetraoctylammonium;

$n \geq 8$, particularly n=8-500 or 100-500; preferably n=150-400;

Alternatively, the sulfonic acid is selected from a perfluorosulfonic acid according to formula (4) and (5):

(4)

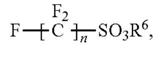

(5)

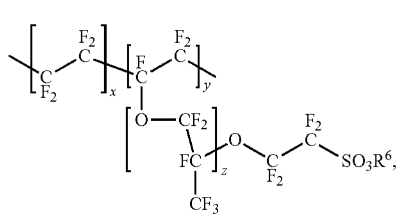

with $R^6$=H, Na, K, Ag, tetrabutylammonium, or tetraoctylammonium;

$n \geq 8$, x=y=50-150, especially 75-125, and z=0, 1, 2, or 3;

corresponding to, e.g., the commercially available Nafion™, Hyflon™, Aquivion™, and 3M™-ionomer. Available materials with typically $R^6$=H can easily be converted into the corresponding salts, comprising, e.g., $R^6$=Na, K, Ag, tetrabutylammonium, or tetraoctylammonium. As described in an example further below, Nafion® perfluorinated resin solution (Cas.: 31175-20-9) is commercially available (e.g., 25 ML) from Sigma Aldrich (SKU-274704).

Thus, for instance, compounds comprising at least 8 carbon atoms, such as, e.g., perfluorooctanesulfonic acid (CAS: 1763-23-1), 1H,1H,2H,2H-perfluorooctanesulfonic acid (CAS: 27619-97-2) or even 8:2 fluorotelomer sulfonate/1H,1H,2H,2H-perfluorodecane-sulfonic acid (CAS: 39108-34-4) or any mixture thereof can be used as well.

Typically, the sulfonic acid is used to catalyse the decomposition of the analyte. A gas guiding system, e.g. a channel, of a sample collecting and analysing device for explosives may comprise Nafion, Hyflon, Aquivion, or 3M™-ionomer, e.g. as a foil, as a tube, or as an inlay of a tube. Advantageously, these materials are thermally stable up to 175° C. and skin-tolerant. These sulfonic acids may also be applied as solution on a microfluidic chip or on the swipe sample material.

The sulfonic acid functions as a catalyst which upon contact with the analyte decomposes the analyte, e.g. into nitric acid. The reaction of the nitric acid with the molecular probe generates a specific fluorescence intensity which is measured.

Commercially available membranes comprising Nafion, Hyflon, Aquivion or 3M™-ionomer can be used as swipe sample material or they can be introduced in a swipe sample heater or into the mouth of a device with a contact heater. Advantageously, then a separate catalyst layer and high temperatures for the decomposition and/or sublimation of the low volatile analytes e.g. ammonium nitrate is not necessary. Further, acrylamido(methyl)propylsulfonic acid, as well as the polymer poly(2-acrylamido-2-methyl-1-propanesulfonic acid may be used for their pronounced hydrophilicity and acidity.

According to an embodiment, the sulfonic acid is selected from a substance according to formula (1) above, wherein independently from each other:

$R^1$, $R^5$=H, Me, Et, F, $CF_3$, Cl, Br, I, $NH_2$, $CO_2H$, $PO_3H_2$, or $SO_3H$;

$R^2$, $R^4$=H, Me, Et, F, $CF_3$, Cl, Br, I, $NH_2$, $CO_2H$, $PO_3H_2$, or $SO_3H$; and $R^3$=H, Me, Et, F, $CF_3$, Cl, Br, I, $NH_2$, $CO_2H$, $PO_3H_2$, or $SO_3H$ $R^6$=H, Na, K, Ag, tetrabutylammonium, tetraoctylammonium, or tetraalkylammonium.

Typically, hygroscopic and water-absorbing materials as well as hydrophobic materials serve as carrier materials for the selected triarylborane dyes and for the selected BODIPY™ dyes. Most of the sulfonic acids used here are crystalline solids. As air humidity increases, they absorb water from the air and pass through the excess water of crystallization into the liquid phase. The catalytic activity of the acid depends on whether it is in liquid or solid form. There are no free protons in solid form. Therefore, the catalytic activity of the acid in solid form is low. In dissolved form, however, free protons are present, which means that the acid has a high catalytic activity. To ensure that the catalytic activity of the acid is not dependent on environmental conditions or that the acid does not crystallize, hydrogel/acid mixtures or a mixture of acid and the corresponding tetrabutylammonium salt (TBA salt) of the acid are used. A mixture of hydrogel/TBA sulfonate/sulfonic acid and porous silica/TBA sulfonate/sulfonic acid is also possible. Hydrogels are known for their ability to absorb water. The TBA salts of the acids are hygroscopic and attract humidity from the environment and thus keep the catalyst layer in liquid form even at higher temperatures.

According to an embodiment, the molecular probe is an organoboron compound, especially a triarylborane dye according to formula (6):

(6)

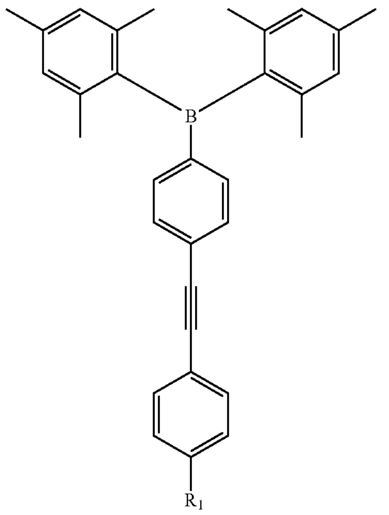

, wherein $R^1$=$NHCH_2CH_2NH_2$, $NHCH_2CH_2NH$(alkyl), $NHCH_2CH_2NHPh$, $NHCH_2CH_2NHAr$, $NHNH_2$, NHNHMe, NHNHPh, NHNHAr, $NHNHCH_2CH_2NH_2$, $NHNHCH_2CH_2NH$(alkyl), $NHNHCH_2CH_2NHPh$, $NHNHCH_2CH_2NHAr$, CO—$NHCH_2CH_2NH_2$, CO—$NHNH_2$, CO—NHNHMe, CO—$NHNHCH_2CH_2NH_2$, CO—$NHNHCH_2CH_2NHPh$, CO—$NHNHCH_2CH_2NHAr$, NH—CO—$NHNH_2$, NHNH—CO—$NHNH_2$, NHNH—CO—$NH_2$, NH—CS—NHNH—CO—Me, NH—CO—NHNH—CO—Me, CO—NHNH—CS—$NH_2$, NH—CS—NHNH—CO-alkyl, CO—NHNH—CS—NH(alkyl),

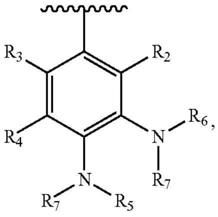

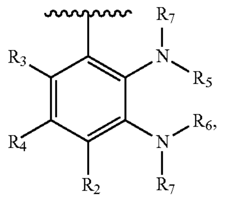

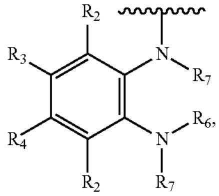

and their meta- and para-regioisomers of the amine groups and

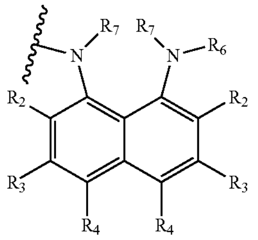

and its regioisomers of the amine groups and $R^2$=H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N(alkyl)_2$, OH, OMe, OiPr, or O(alkyl), $R^3$=H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N(alkyl)_2$, OH, OMe, OiPr, or O(alkyl), $R^4$=H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N(alkyl)_2$, OH, OMe, OiPr, or O(alkyl), $R^5$=H, Me, Et, Pr, alkyl, phenyl, benzyl, aryl, $CF_3$, CO—Me, CO-alkyl, CO-aryl, $NH_2$, OMe, OiPr, or O(alkyl), $R^6$=H, Me, Et, Pr, alkyl, phenyl, benzyl, aryl, $CF_3$, CO—Me, CO-alkyl, CO-aryl, $NH_2$, OMe, OiPr, or O(alkyl), and $R^7$=H.

According to a modification of the embodiment above, between the residue $R^1$ and the adjacent phenyl group a phenyl group, a double bond, a triple bond, a $CH_2$-group or a $CH_2CH_2$-group can be formed. According to a modification of the embodiment above, between the phenylenediamine groups respectively the naphthylenediamine groups and the adjacent phenyl group a carbonyl group and a thiocarbonyl group can be formed. Further, instead of the triple bond shown in formula (6), also a double bond, a dienyl group, a diyne group, a triyne group, a phenylene group, an aryl group or a simple sigma bond can be formed.

According to an embodiment, the organoboron compound, i.e. the triarylborane dye is selected according to formula (7) indicated below:

(7)

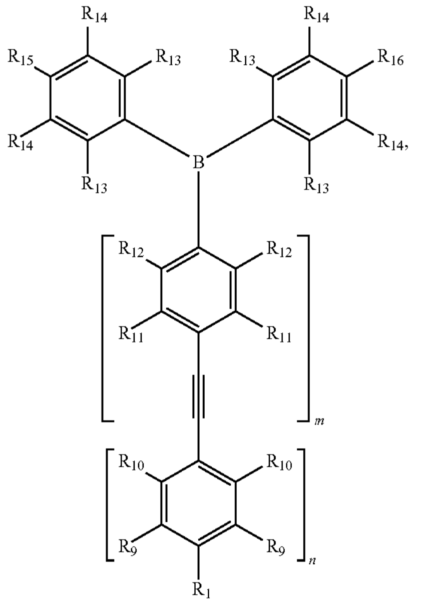

wherein $R_1$=$NHCH_2CH_2NH_2$, $NHCH_2CH_2NH(alkyl)$, $NHCH_2CH_2NHPh$, $NHCH_2CH_2NHAr$, $NHNH_2$, NHNHMe, NHNHPh, NHNHAr, $NHNHCH_2CH_2NH_2$, $NHNHCH_2CH_2NH(alkyl)$, $NHNHCH_2CH_2NHPh$, $NHNHCH_2CH_2NHAr$, CO—$NHCH_2CH_2NH_2$, CO—$NHNH_2$, CO—NHNHMe, CO—$NHNHCH_2CH_2NH_2$, CO—$NHNHCH_2CH_2NHPh$, CO—$NHNHCH_2CH_2NHAr$, NH—CO—$NHNH_2$, NHNH—CO—$NHNH_2$, NHNH—CO—$NH_2$, NH—CS—NHNH—CO—Me, NH—CO—NHNH—CO—Me, CO—NHNH—CS—$NH_2$, NH—CS—NHNH—CO-alkyl, CO—NHNH—CS—NH(alkyl),

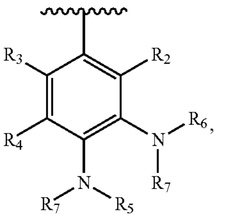

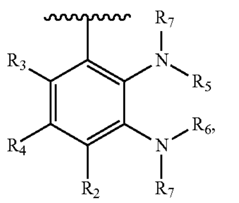

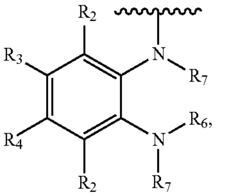

and their meta- and para-regioisomers of the amine groups and

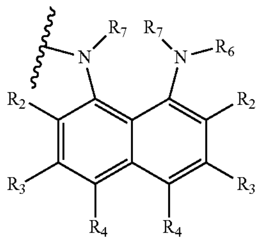

and its regioisomers of the amine groups and $R_2$=H, Me, alkyl, phenyl, benzyl, aryl, F, Cl, Br, I, $CF_3$, $NH_2$, $NO_2$, $CO_2H$, $CH_2OH$, $CH_2O(alkyl)$, $CH_2NMe_2$, $CH_2N(alkyl)_2$, OH, OMe, OiPr, or O(alkyl), $R_3$=H, Me, alkyl, phenyl, benzyl, aryl, F, Cl, Br, I, $CF_3$, $NH_2$, $NO_2$, $CO_2H$, $CH_2OH$, $CH_2O(alkyl)$, $CH_2NMe_2$, $CH_2N(alkyl)_2$, OH, OMe, OiPr, or O(alkyl), $R_4$=H, Me, alkyl, phenyl, benzyl, aryl, F, Cl, Br, I, $CF_3$, $NH_2$, $NO_2$, $CO_2H$, $CH_2OH$, $CH_2O(ALKYL)$, $CH_2NMEZ$, $CH_2N(ALKYL)_2$, OH, OME, OIPR, OR O(ALKYL), $R_5$=H, Me, Et, Pr, alkyl, phenyl, benzyl, aryl, $CF_3$, CO—Me, CO-alkyl, CO-aryl, $NH_2$, OMe, OiPr, or O(alkyl), $R_6$=H, Me, Et, Pr, alkyl, phenyl, benzyl, aryl, $CF_3$, CO—Me, CO-alkyl, CO-aryl, $NH_2$, OMe, OiPr, or O(alkyl), $R_7$=H, and with n, m=0, 1, 2, 3, or 4.

According to a modification of the embodiment above, between the residue $R_1$ and the adjacent phenyl group a phenyl group, a double bond, a triple bond, a $CH_2$-group or a $CH_2CH_2$-group can be formed. According to a modification of the embodiment above, between the phenylenediamine groups respectively the naphthylenediamine groups and the adjacent phenyl group a carbonyl group and a thiocarbonyl group can be formed. Further, instead of the triple bond shown in formula (7), also a double bond, a dienyl group, a diyne group, a triyne group, a phenylene group, an aryl group or a simple sigma bond can be formed.

$R_9$, $R_{10}$, $R_{11}$, $R_{12}$, $R_{13}$, $R_{14}$, $R_{15}$, $R_{16}$=H, Me, alkyl, phenyl, benzyl, aryl, F, Cl, Br, I, $CF_3$, $CH_2OH$, $CH_2O(alkyl)$, $CH_2NMe_2$, $CH_2Nalkyl_2$, $CH_2P(tBu)_2$, $CH_2P$ $(alkyl)_2$, OMe, OiPr, or O(alkyl), or $R_9$, $R_{10}$, $R_{11}$, $R_{12}$, $R_{13}$, $R_{14}$ are as indicated above, and $R_{15}$, $R_{16}$=H, F, Cl, Br, I, Me, alkyl, phenyl, aryl, vinyl, ethinyl, alkynyl, $CF_3$, $NMe_2$, $NPh_2$, or $B(Mes)_2$. Herein, "Mes" stands for mesityl (cf. https://www.wikidata.org/wiki/Q1898549).

Alternatively, $R_9$, $R_{10}$, $R_{11}$, $R_{12}$, $R_{13}$, $R_{14}$ are as indicated above, and $R_{15}$, $R_{16}$ =
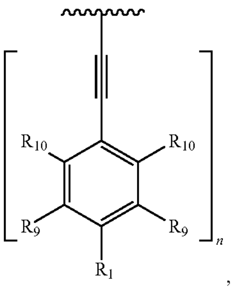
, with n, m=0, 1, 2, 3, or 4;

According to a modification of the embodiments listed above, between the residue $R_1$ and the adjacent phenyl group a double or a triple bond or a —$CH_2$— or a —$CH_2CH_2$— can be formed. Further, instead of the triple bond shown in formula (7), also a double bond, a dienyl group, a diyne group, a triyne group, a phenylene group, an aryl group or a simple sigma bond can be formed.

According to an embodiment the organoboron compound, i.e. the triarylborane dye is selected among a substance according to formula (8), (9) and (10) as indicated below (8)
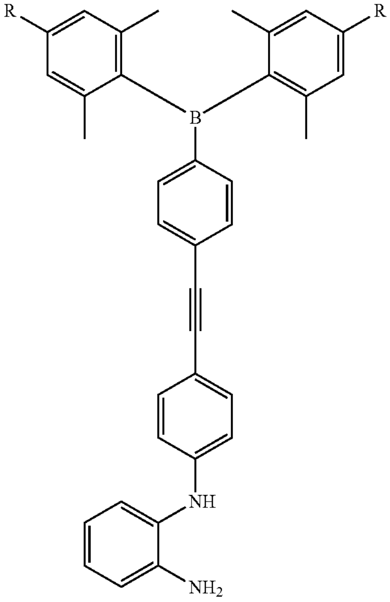

-continued (9)
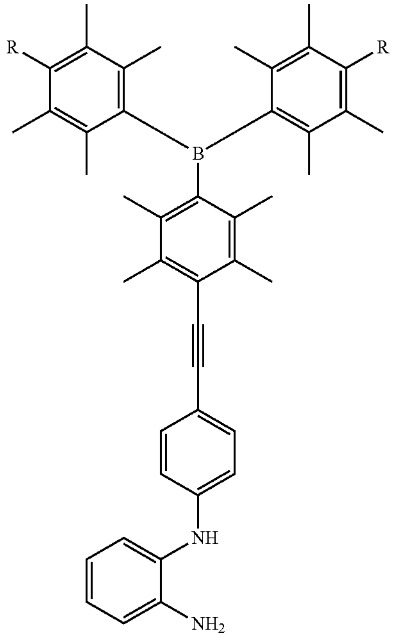

(10)
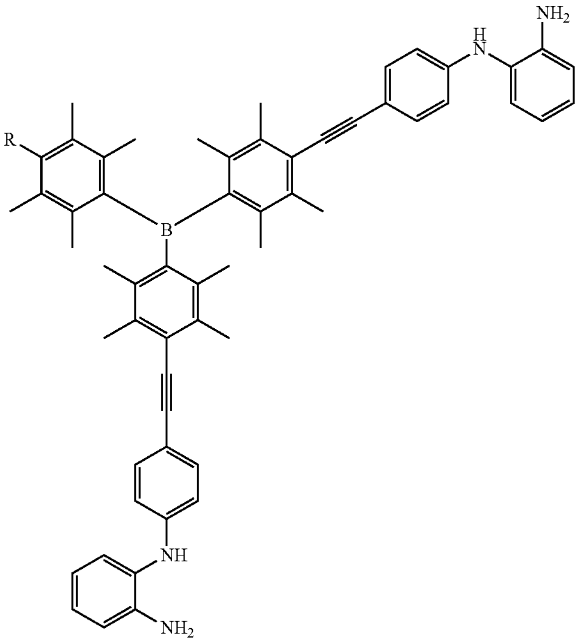

with

R=H, F, Cl, Br, I, Me, alkyl, phenyl, aryl, vinyl, ethinyl, alkynyl, $CF_3$, $NMe_2$, $NPh_2$, or $B(Mes)_2$.

The methyl groups in ortho position to the borane group enhance the stability of the dye by protecting the borane center from hydrolysis and oxidation. The ortho-phenylene-diamine group is not protected thus it can easily react with nitric oxides e.g. NO, $NO_2$ or nitric acid and nitrous acid to a corresponding triazole or nitroso compounds (see below) or to an azide in case of hydrazines.

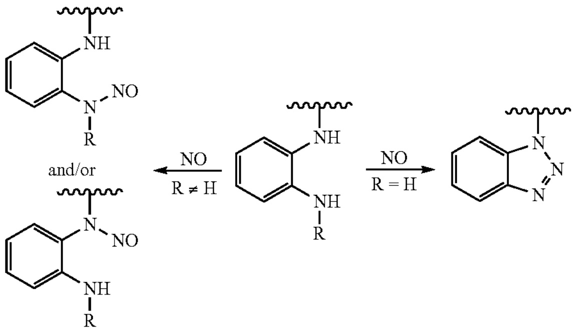

Schematic of reaction of ortho-phenylenediamines with nitric oxides.

According to an embodiment the molecular probe is an organoboron compound, i.e. the triarylborane dye is a substance according to formula (11):

(11)

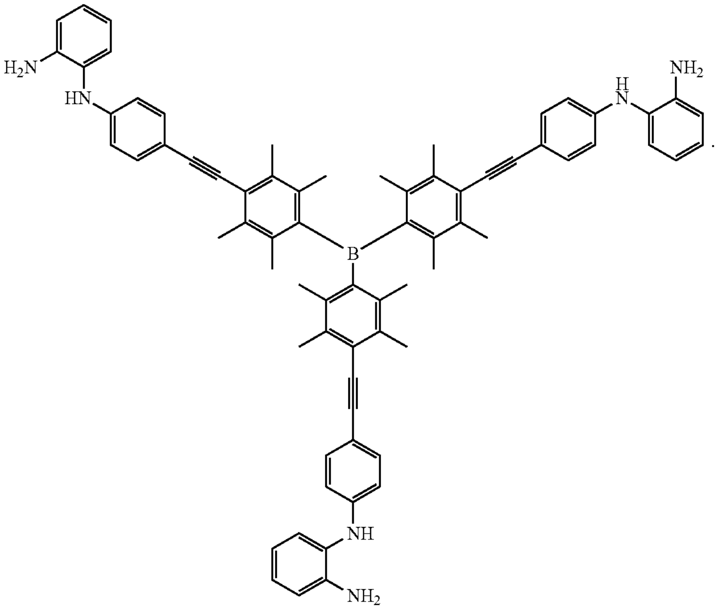

According to an embodiment the carrier material comprises a hydrophilic polymer, an amphiphilic macromolecule, a porous silica material or any mixture thereof.

According to an embodiment, the molecular probe is another organoboron compound, in particular a BODIPY™ (boron-dipyrromethene) selected from a substance according to formula (12):

(12)

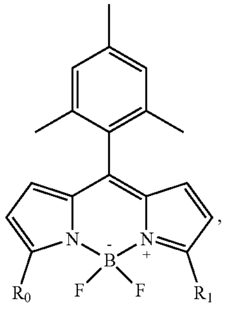

wherein $R_1$=$NHCH_2CH_2NH_2$, $NHCH_2CH_2NH$(alkyl), $NHCH_2CH_2NHPh$, $NHCH_2CH_2NHAr$, $NHNH_2$, NHNHMe, NHNHPh, NHNHAr, $NHNHCH_2CH_2NH_2$, $NHNHCH_2CH_2NH$(alkyl), $NHNHCH_2CH_2NHPh$, $NHNHCH_2CH_2NHAr$, CO—$NHCH_2CH_2NH_2$, CO—$NHNH_2$, CO—NHNHMe, CO—$NHNHCH_2CH_2NH_2$, CO—$NHNHCH_2CH_2NHPh$, CO—$NHNHCH_2CH_2NHAr$, NH—CO—$NHNH_2$, NHNH—CO—$NHNH_2$, NHNH—CO—$NH_2$, NH—CS—NHNH—CO—Me, NH—CO—NHNH—CO—Me, CO—NHNH—CS—$NH_2$, NH—CS—NHNH—CO-alkyl, CO—NHNH—CS—NH(alkyl),

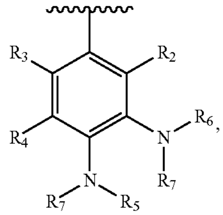

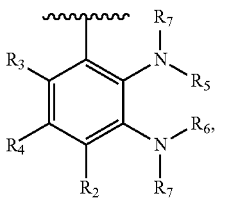

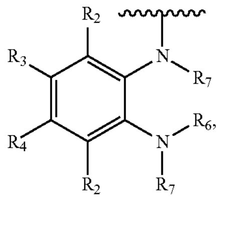

and their meta- and para-regioisomers of the amine groups and

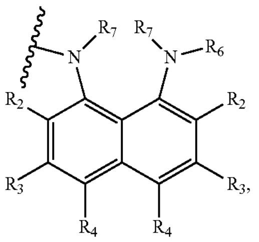

and its regioisomers of the amine groups and $R_2$=H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N$(alkyl)$_2$, OH, OMe, OiPr, or O(alkyl), $R_3$=H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N$(alkyl)$_2$, OH, OMe, OiPr, or O(alkyl), $R_4$=H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N$(alkyl)$_2$, OH, OMe, OiPr, or O(alkyl), $R_5$=H, Me, Et, Pr, alkyl, phenyl, benzyl, aryl, $CF_3$, CO-Me, CO-alkyl, CO-aryl, $NH_2$, OMe, OiPr, or O(alkyl), $R_6$=H, Me, Et, Pr, alkyl, phenyl, benzyl, aryl, $CF_3$, CO—Me, CO-alkyl, CO-aryl, $NH_2$, OMe, OiPr, or O(alkyl), $R_7$=H, and $R_0$=$NHCH_2CH_2NH_2$, $NHCH_2CH_2NH$(alkyl), $NHCH_2CH_2NHPh$, $NHCH_2CH_2NHAr$, $NHNH_2$, NHNHMe, NHNHPh, NHNHAr, $NHNHCH_2CH_2NH_2$, $NHNHCH_2CH_2NH$(alkyl), $NHNHCH_2CH_2NHPh$, $NHNHCH_2CH_2NHAr$, CO—$NHCH_2CH_2NH_2$, CO—$NHNH_2$, CO—NHNHMe, CO—$NHNHCH_2CH_2NH_2$, CO—$NHNHCH_2CH_2NHPh$, CO—$NHNHCH_2CH_2NHAr$, NH—CO—$NHNH_2$, NHNH—CO—$NHNH_2$, NHNH—CO—$NH_2$, NH—CS—NHNH—CO—Me, NH—CO—NHNH—CO—Me, CO—NHNH—CS—$NH_2$, NH—CS—NHNH—CO-alkyl, CO—NHNH—CS—NH(alkyl), H, Me, Et, alkyl, phenyl, benzyl, aryl, styryl, vinyl, alkynyl, F, Cl, Br, I, $CF_3$, CN, $NO_2$, $CO_2H$, $CO_2Me$, O—CO—Me, O—CO-alkyl, O—CO-aryl, O—CO-(phenylenediamine), OH, OMe, O(iPr), or O(alkyl), According to a modification of the embodiment above, between the residue $R_0$ and/or $R_1$ and the adjacent BODIPY™ structure a phenyl group, a double bond, a triple bond, a styryl group, a phenylacetylene group, a $CH_2$-group or a $CH_2CH_2$-group can be formed.

According to a further modification, between a phenylenediamine group or a naphthylenediamine group of the residue $R_1$ and the adjacent BODIPY™ group a carbonyl group is formed.

According to an embodiment, the molecular probe is a BODIPY™ dye selected from a substance according to formula 13:

(13)

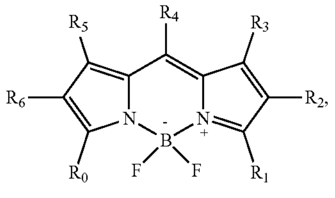

wherein $R_1$=$NHCH_2CH_2NH_2$, $NHCH_2CH_2NH$(alkyl), $NHCH_2CH_2NHPh$, $NHCH_2CH_2NHAr$, $NHNH_2$, NHNHMe, NHNHPh, NHNHAr, $NHNHCH_2CH_2NH_2$, $NHNHCH_2CH_2NH$(alkyl), $NHNHCH_2CH_2NHPh$, $NHNHCH_2CH_2NHAr$, CO—$NHCH_2CH_2NH_2$, CO—$NHNH_2$, CO—NHNHMe, CO—$NHNHCH_2CH_2NH_2$, CO—$NHNHCH_2CH_2NHPh$, CO—$NHNHCH_2CH_2NHAr$, NH—CO—$NHNH_2$, NHNH—CO—$NHNH_2$, NHNH—CO—$NH_2$, NH—CS—NHNH—CO—Me, NH—CO—NHNH—CO—Me, CO—NHNH—CS—$NH_2$, NH—CS—NHNH—CO-alkyl, CO—NHNH—CS—NH(alkyl),

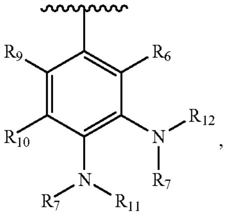
,
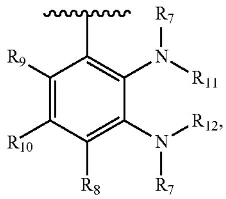

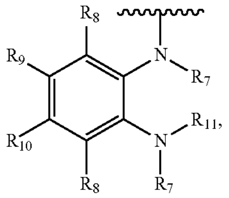

and their meta- and para-regioisomers of the amine groups and

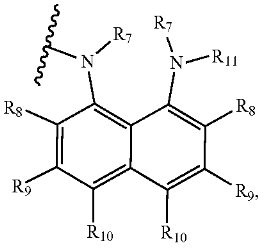

and its regioisomers of the amine groups and wherein $R_7$=H, $R_8$=H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N$(alkyl)$_2$, OH, OMe, OiPr, or O(alkyl), $R_9$=H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N$(alkyl)$_2$, OH, OMe, OiPr, or O(alkyl), $R_{10}$=H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N$(alkyl)$_2$, OH, OMe, OiPr, or O(alkyl), $R_{11}$=H, Me, Et, Pr, alkyl, phenyl, benzyl, aryl, $CF_3$, CO-Me, CO-alkyl, CO-aryl, $NH_2$, OMe, OiPr, or O(alkyl);

$R_{12}$=H, Me, Et, Pr, alkyl, phenyl, benzyl, aryl, $CF_3$, CO-Me, CO-alkyl, CO-aryl, $NH_2$, OMe, OiPr, or O(alkyl);

$R_0$=$NHCH_2CH_2NH_2$, $NHCH_2CH_2NH$(alkyl), $NHCH_2CH_2NHPh$, $NHCH_2CH_2NHAr$, $NHNH_2$, NHNHMe, NHNHPh, NHNHAr, $NHNHCH_2CH_2NH_2$, $NHNHCH_2CH_2NH(alkyl)$, $NHNHCH_2CH_2NHPh$, $NHNHCH_2CH_2NHAr$, CO—$NHCH_2CH_2NH_2$, CO—$NHNH_2$, CO—NHNHMe, CO—$NHNHCH_2CH_2NH_2$, CO—$NHNHCH_2CH_2NHPh$, CO—$NHNHCH_2CH_2NHAr$, NH—CO—$NHNH_2$, NHNH—CO—$NHNH_2$, NHNH—CO—$NH_2$, NH—CS—NHNH—CO—Me, NH—CO—NHNH—CO-Me, CO—NHNH—CS—$NH_2$, NH—CS—NHNH—CO-alkyl, CO—NHNH—CS—NH(alkyl), H, Me, Et, alkyl, phenyl, benzyl, aryl, styryl, vinyl, alkynyl, F, Cl, Br, I, $CF_3$, CN, $NO_2$, $CO_2H$, $CO_2Me$, O—CO—Me, O—CO-alkyl, O—CO-aryl, O—CO-(phenylenediamine), OH, OMe, O(iPr), or O(alkyl);

$R_2$, $R_3$, $R_5$, $R_6$═H, Me, Et, alkyl, phenyl, benzyl, aryl, 2-pyridyl, 3-vinyl, alkynyl, F, Cl, Br, I, $CF_3$, $CH_2OH$, $CH_2O(alkyl)$, $CH_2NMe_2$, $CH_2N(alkyl)_2$, OMe, OiPr, or O(alkyl), $R_4$═mesityl, 2-alkylphenyl, 2-tolyl, 3-tolyl, 2,6-xylyl, 2,5-xylyl, 2,4-xylyl, 2,3-xylyl, 2,6-dichlorophenyl, 2,3,6-trichlorophenyl, 2,4,6-trichlorophenyl, 2,6-difluorophenyl, 2,3,6-trifluorophenyl, 2,4,6-trifluorophenyl, Ph-$B(Mes)_2$, or aryl-$B(Mes)_2$.

According to a modification of the embodiment above, between the residue $R_0$ and/or $R_1$ and the adjacent BODIPY™ structure a phenyl group, a double bond, a triple bond, a styryl group, a phenylacetylene group, a $CH_2$-group or a $CH_2CH_2$-group can be formed. According to a modification of the embodiment above, between the phenylenediamine groups respectively the naphthylenediamine groups and the adjacent BODIPY™ group a carbonyl group and a thiocarbonyl group can be formed.

According to an embodiment the BODIPY™ dye is selected among a substance according to formula (14), (15) and (16) as indicated below (14)

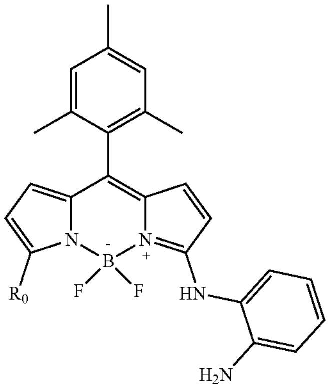

,

-continued (15)

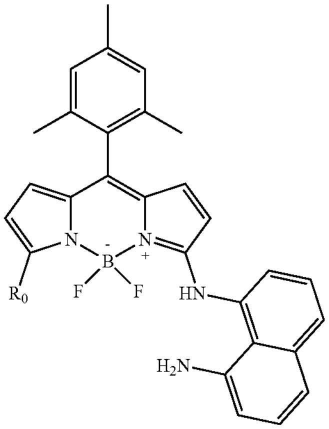

, (16)

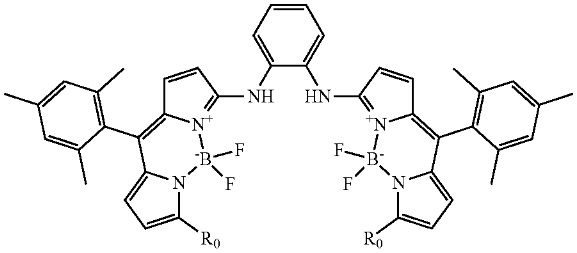

with $R_0$═H, Me, Et, alkyl, phenyl, benzyl, aryl, styryl, vinyl, alkynyl, F, Cl, Br, I, $CF_3$, CN, $NO_2$, $CO_2H$, $CO_2Me$, OH, OMe, O(iPr), or O(alkyl).

The triarylborane dye according to formula (8) and the BODIPY™ dye according to formula (14) are both used for the detection of nitrate explosives. Whereas their general structure is not identical, they are both boron-based dyes that carry the same type of reaction sites selective to the analyte. Furthermore, the mentioned triarylborane dye can be excited at a wavelength of 365 nm, whereas the mentioned BODIPY™ dye has an excitation wavelength of 510 nm. Thus, both dyes together enable a sensitive detection of nitrate-based explosives, using two different excitation wavelengths.

Advantageously, the 1,2-diamino group ensures the cyclisation reaction with nitric oxides to a triazole and enhances the selectivity to nitrate based explosives.

Advantageously, the amino group ensures the reaction with nitric oxides to an amino nitrous oxide and enhance the selectivity to nitrate-based explosives.

According to an embodiment the carrier material comprises a hydrophobic polymer or a hydrophobic polymer, an amphiphilic macromolecule, porous silica material or their mixture.

Advantageously, commercially available substances can be used at low costs. For instance, polystyrene could be used as carrier material.

According to an embodiment the hydrophilic and hydrophobic polymeric carrier materials are selected from a hydrophilic polyurethane, an aliphatic polyether-based polyurethane, or a block copolymer comprising at least a hydrophilic block and polystyrene e.g. as polyHIPE (Porous Polymers Synthesized within High Internal Phase Emulsions).

Advantageously, the porous hydrophilic polyurethane carrier materials for the triarylborane dyes and BODIPY™ dyes can absorb the volatile and hydrophilic nitric oxides, nitric acid and nitrous acid. This characteristic prolongs the maintenance time of the strong nitrogen-based acids in or on the sensor layer.

According to an embodiment suitable block copolymers can be selected, e.g., from nonionic triblock copolymers composed of poly(propylene oxide) and poly(ethylene oxide) units which are also known as poloxamers.

Advantageously, the poloxamers have low melting points. Thus, at temperatures above 50° C. they form liquids which can better uptake nitric acid than solids.

Trade names of suitable hydrophilic polyurethanes, especially of ether-based hydrophilic polyurethanes, are e.g., Hydromed™-D1, -D2, -D3, -D4, -D6, -D640, Hydromed™-D7, and HydroSlip C. Another hydrophilic thermoplastic polyurethane elastomer suitable as carrier material is, e.g., HydroThane™. Trade names of other hydrophilic, especially of aliphatic polyether-based thermoplastic polyurethanes which are suitable as carrier materials are Tecoflex™ and Tecophilic™.

Advantageously, these hydrophilic polymers are stable under UV-illumination and do not show yellowing by aging or heating. Furthermore, they readily form hydrogels by rapidly absorbing water. These polymers and resulting hydrogels also easily absorb nitric acid. Surprisingly, they withstand possible oxidation by nitric acid which ensures their suitability as inert carrier materials for the analytes and their reaction products. Polymers of the HydroMed D series have a water content of 30 to 95% and comprise a linear expansion from 10 to 180%. Advantageously, they provide a good adsorption and absorption capacity of a corresponding sensor layer for hydrogen peroxide and provide certain porosity of the sensor layer after drying, i.e. an enhanced surface for adsorption of the analytes and their reaction products. For polymers of the HydroMed-D Series the following weight ratios (polymer/EtOH/$H_2O$) have been proven to be suitable: 1.0-2.0 g/20-25 g/2-3 g. In particular, weight ratios of 2.0 g of the polymer; 22 g EtOH; and 2.5 g $H_2O$ can be used.

Trade names of poloxamers are, e.g., Synperonic®, Pluronic®, and Kolliphor®. In particular, the hydrophilic polymer may be selected, e.g., from poloxamer 188, Pluronic® F-68, Pluronic® F-108, poloxamer 407, Pluronic® F-127, and Pluronic® P-123. From experimental results follows that these polymers are inferior in comparison to, e.g., polymers of the Hydromed™—series if used as carrier substances in the suggested sensor layer.

According to an embodiment other hydrophilic polymers suitable as carrier material are poly(ethylene glycols) having a molecular weight of $M_n$=35,000, 20,000 12,000, 10,000, etc., Therein, and further below, $M_n$ is the total weight of all the polymer molecules in a given sample, divided by the total number of polymer molecules in the sample.

Other suitable hydrophilic polymers are poly(ethylene glycol) methyl ether ($M_n$=35,000, 20,000, 12,000, 10,000, etc.), poly(ethylene glycol) dimethyl ether ($M_n$=35,000, 20,000, 12,000, 10,000, etc.), poly(ethylene glycol) dialkyl ether ($M_n$=35,000, 20,000, 12,000, 10,000, etc.), poly(ethylene glycol) diacrylate ($M_n$=35,000, 20,000, 12,000, 10,000, 6,000 etc.), poly(ethylene glycol) dimethacrylate ($M_n$=35,000, 20,000, 12,000, 10,000, 6,000 etc.), polyvinyl alcohol, polyvinyl pyrrolidone, poly(diallyldimethylammonium chloride) and co-polymers comprising at least one of the above.

Further, their mixtures with porous materials, like, e.g., fumed silica and the hydrophobic materials, like, e.g., polystyrene, poly HIPE, polystyrene-co-methylmetharylate, polymethacrylate, polyalkylmethacrylate, polyphenylmethacrylate, polyphenylenether, polybenzylmethacrylate can be used as carrier material.

The proposed sulfonic acids in the catalyst layer, on the wipe sample material or on the wipe sample heater decompose the nitrates into nitric acid, nitrous acid and nitric oxides.

This allows detecting even small quantities of nitrates (<<100 ng) without the measurement signal quickly recovering or decreasing.

Typical layer thicknesses of catalyst and sensor films are in the micrometer to millimeter range. The larger the sensor and catalyst surface, the better the absorption of the analytes.

Different hydrophilicity and hygroscopicity can support the adsorption and absorption of nitrates, nitric acid, nitrous acid and nitric oxides-by the analyte sensitive layer and increase its sensitivity.

Different hydrophobicity can support the adsorption and absorption of nitrates, nitric acid, nitrous acid and nitric oxides-by the analyte sensitive layer and increase its selectivity.

As to the selection of the substrate it is important that it is not fluorescent, or that the fluorescence can be "erased", e.g. by UV irradiation. If a polymer is used as the substrate, e.g., a cyclic olefin polymer (COP) (see e.g.: Microfluid. Nanofluid. 2010, 9, 145-161), a range of manufacturers offers suitable materials under various brand names (e.g. Apel, Arton, Topas, Zeonex and Zeonor). Some of these (Apel and Topas) are made from more than one kind of monomer and are therefore also designated as cyclic olefin copolymers (COCs), which are fluorescent. However, their fluorescence can be erased upon UV irradiation. The substrate material is selected to be heat resistant at least up to 70° C. Therefore, for polymers, the glass transition temperature ($T_g$) is highly important and should be ≥70° C.

According to an embodiment a shape of the substrate encompasses a slide, a plate, a disc, a wall of a channel, a tube, a pipe, a capillary, a porous solid—e.g. a sintered glass frit, a sheet, a slab, a foil, a paper, a grid, a net, a woven or an unwoven textile, an open porous sponge, a thread, a filament, a wire, a rod or a stick.

According to an embodiment the substrate is selected from a material which is optically transparent in a wavelength range between 350-700 nm, wherein "optically transparent" means "comprising a transmittance of at least 50%".

According to an embodiment a method of fabricating an analyte sensitive layer is suggested. The method comprises providing:

- a triarylborane dye and/or a BODIPY™ dye, and
- a hydrophilic or hydrophobic carrier material,
- wherein the triarylborane dye and/or the BODIPY™ dye are homogenously mixed and deposited as a sensor layer on a substrate,
- wherein the carrier material and/or a mixing ratio of the triarylborane dye and/or the BODIPY™ dye with the carrier material is selected such as to form upon drying a free-standing film (foil);
- applying on a substrate surface a mixture of the triarylborane dye and/or the BODIPY™ dye, and the carrier material;
- drying the mixture; and
- removing the free-standing film (foil) from the template.

Advantageously, the substrate surface belongs to the microfluidic system, i.e. the lab-on-a-chip, so after drying the free-standing film is not removed, and the chip can be used with a detector and a light source.

According to an embodiment the substrate is selected from a cyclic olefin polymer (COP), particularly, from a cyclic olefin copolymer (COC), and the step "removing the free-standing film (foil) from the template" is omitted.

Advantageously, the mentioned above microfluidic system comprising at least a channel for delivering a gaseous analyte to the analyte sensitive layer is provided. The microfluidic system can easily be prepared, e.g. by hot embossing or injection molding and subsequent deposition of an analyte sensitive layer, e.g., by drop coating. Channel width and depth, as well as the size of reservoirs (cavities) which are connected to channels or interconnected by channels can easily be selected such as to allow a lateral flow of a gas stream which carries the analyte to the analyte sensitive layer. Such microfluidic systems, i.e. ready-to-use-lab-on-a-chip systems are easily to prepare and can be stored as disposables for already existing optical equipment, e.g., portable readers. If the template is a constituent of a microfluidic system, the above step of removing the free-standing film from the template is omitted.

According to an embodiment a method of selective detection of an analyte, selected from nitrates, nitric acid, nitrous acid and nitric oxides is suggested. The method comprises:

Providing an analyte sensitive layer according to any of the corresponding embodiments described above or a fluorescence indicator according to the description above, comprising the analyte sensitive layer.

Directing a fluid stream comprising vaporized or gaseous analyte on the analyte sensitive layer, wherein the fluid is preferably air or an inert gas (e.g. nitrogen) of a temperature within a range from 15-200° C., preferably of 20-100° C. In particular, the temperature at the inlet of the detector is 150-180° C. (depending on a current measurement mode) and the chip is heated to 50-80° C. In view thereof, the temperature of the chip should be within 50-100° C.

Exposing the analyte sensitive layer to an excitation light, i.e. directing an excitation light through the sensor layer, thus exciting a fluorescent compound which is formed within (on) the analyte sensitive layer upon interaction with the analyte.

Measuring a fluorescence intensity over a time interval of <10 s (typically a fluorescence increase).

Detecting at least one of the analytes qualitatively and/or quantitatively.

Advantageously, at low temperatures the sensor layer can uptake more volatile nitric acids and oxides, which can react with the triarylboranes in the sensor layer.

Each embodiment described above may be combined with any other embodiment or embodiments unless clearly indicated to the contrary.

A full and enabling disclosure of the present invention, including the best mode thereof, to one of ordinary skill in the art, is set forth more particularly in the remainder of the description including reference to the accompanying figures.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification (above and below) and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Figure 2:
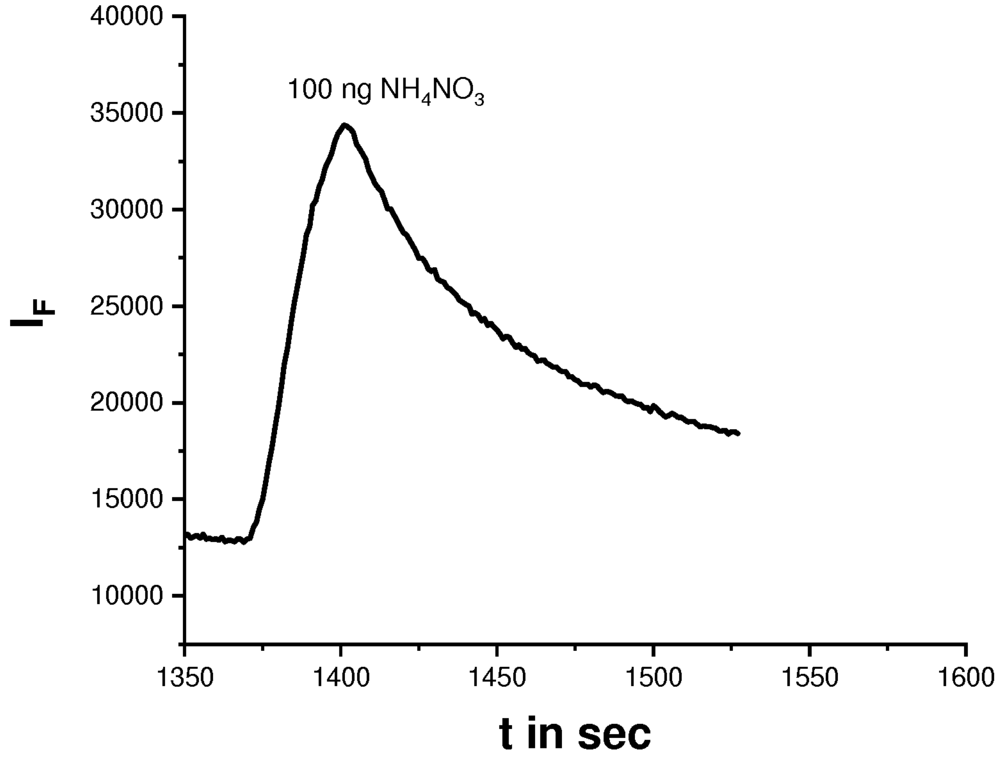
FIG. 2 also shows the fluorescence intensity of the sensor of example 1 (the catalyst Nafion is drop-coated in the channel right before the sensor layer).
Figure 3:
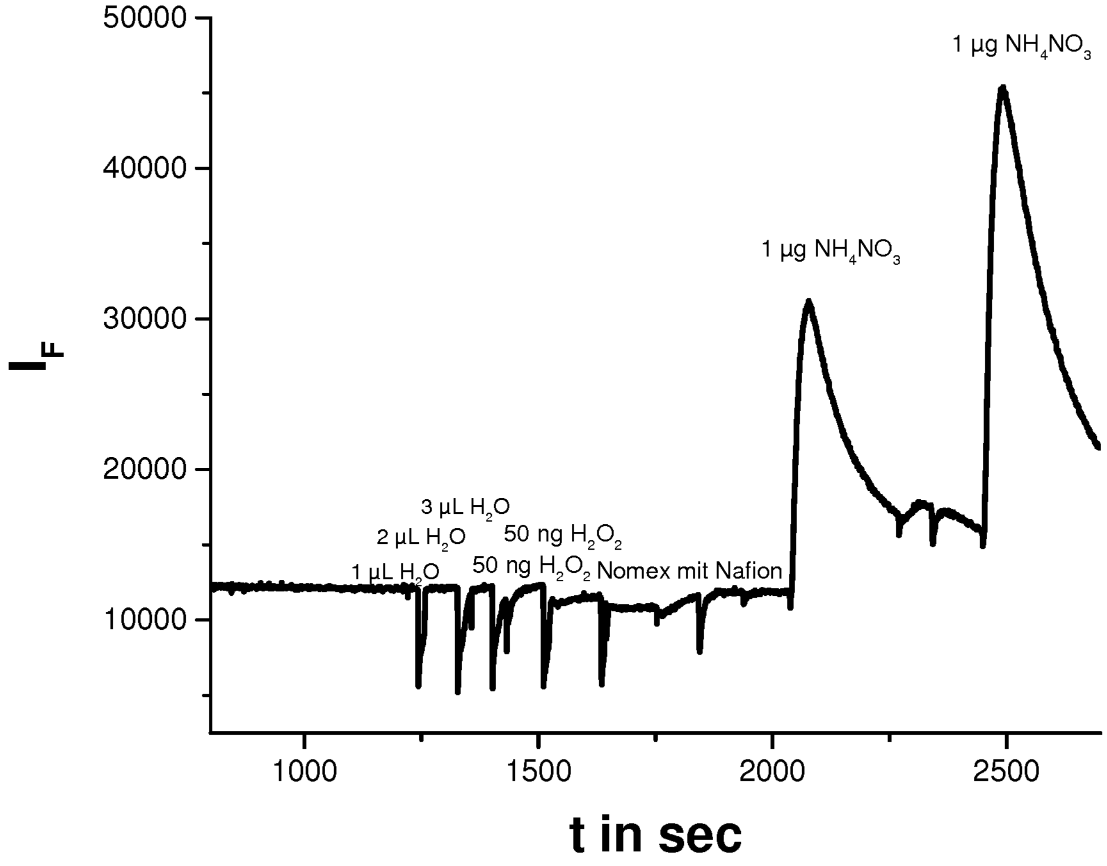
FIG. 3 shows the fluorescence intensity of the sensor of example 2 (the catalyst Nafion is drop-coated on the Nomex foil).

FIG. 1 shows the fluorescence intensity of the sensor of example 1 (the catalyst Nafion is drop-coated in the channel right before the sensor layer). 100 ng $NH_4NO_3$ were detected, exemplified by an increase in fluorescence intensity. In particular, 2 μL Nafion have been placed upstream to the sensor layer, acting as catalyst. Then, 1 μL of a $NH_4NO_3$ solution in methanol (0.1 mg/1 mL) was put on a Teflon strip and measured after a drying period of 2 min. An increase in fluorescence was observed. FIG. 2 also shows the fluorescence intensity of the sensor of example 1 (the catalyst Nafion is drop-coated in the channel right before the sensor layer). 100 ng $NH_4NO_3$ were measured, which show a significant fluorescence increase. FIG. 3 shows the fluorescence intensity of the sensor of example 2 (the catalyst Nafion is drop-coated on the Nomex foil). First, 1, 2 and 3 μL $H_2O$ were measured, showing a slight decrease in fluorescence. Twice, 50 ng $H_2O_2$ in 1 μL $H_2O$ were measured, showing also a slight decrease in fluorescence. The wiping material Nomex coated with 3 μL Nafion also shows a slight decrease in fluorescence.

Figure 4:
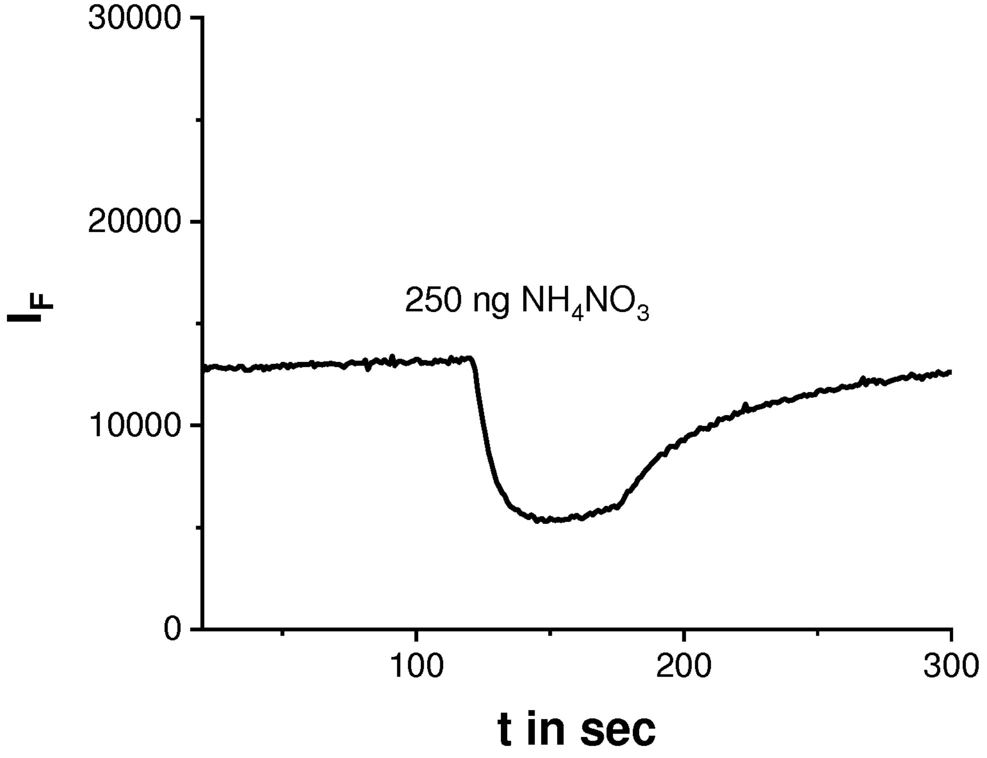
FIG. 4 shows the fluorescence intensity of the sensor of example 3 (the catalyst Nafion is drop-coated in the channel right before the sensor layer).
Figure 5:
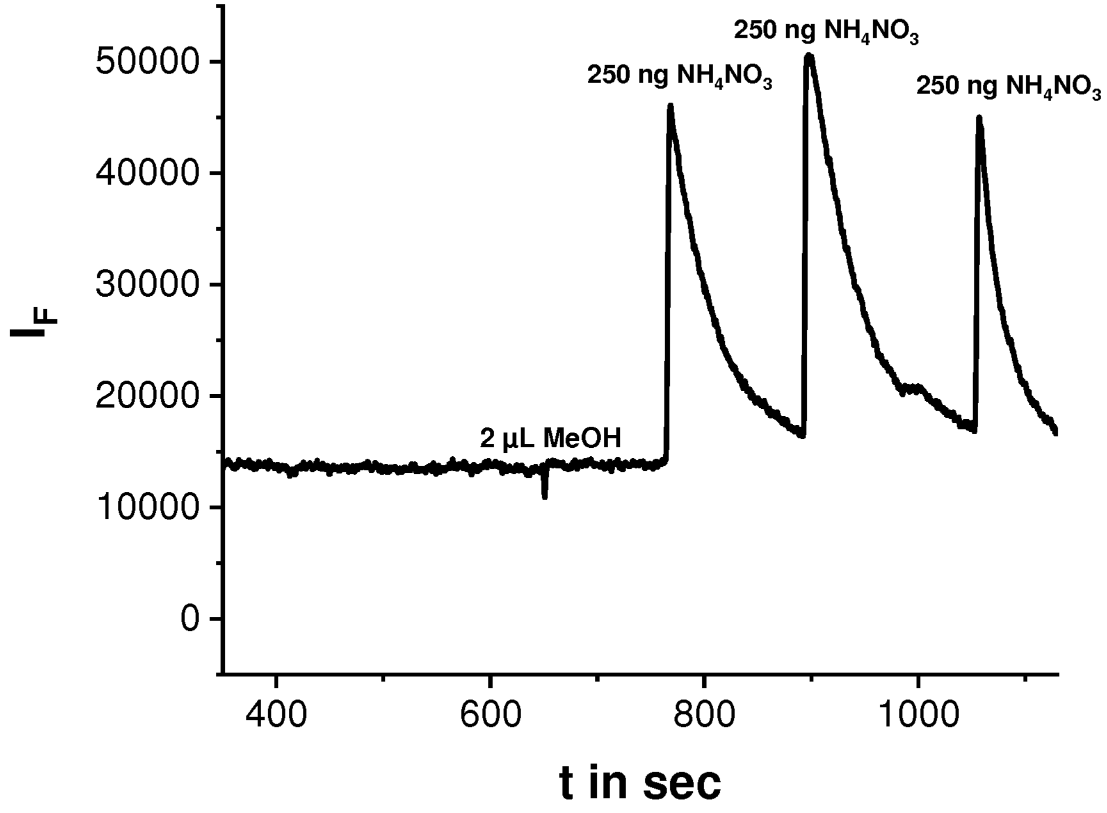
FIG. 5 shows the fluorescence intensity of the sensor of example 4 (the catalyst Nafion is drop-coated on a Teflon foil).
Figure 6:
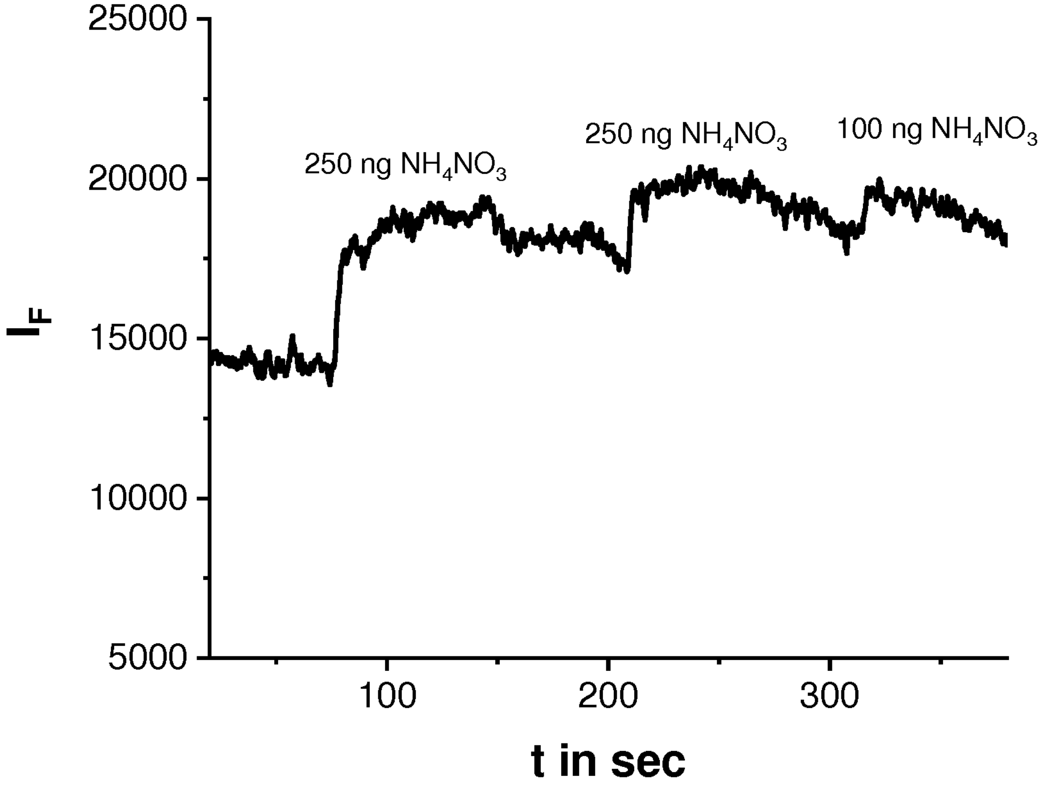
FIG. 6 shows the fluorescence intensity of the sensor layer of example 5 (the catalyst Nafion is drop-coated on a Teflon foil).
Figure 7:
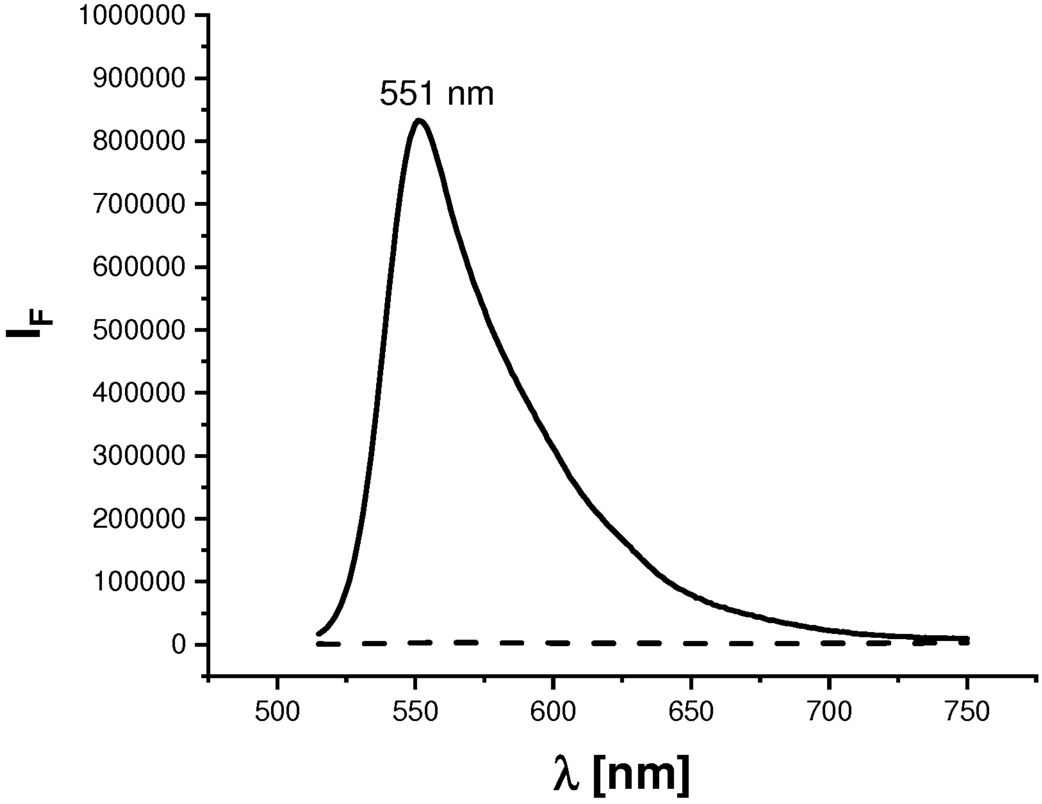
FIG. 7 shows the fluorescence spectra of a BODIPY™ dye according to formula (14) with R0═Cl; further termed compound (14') before and after reaction with tert-butylnitrite (TBN) as NOx source at an excitation wavelength of 510 nm in toluene (example 7).
Figure 8:
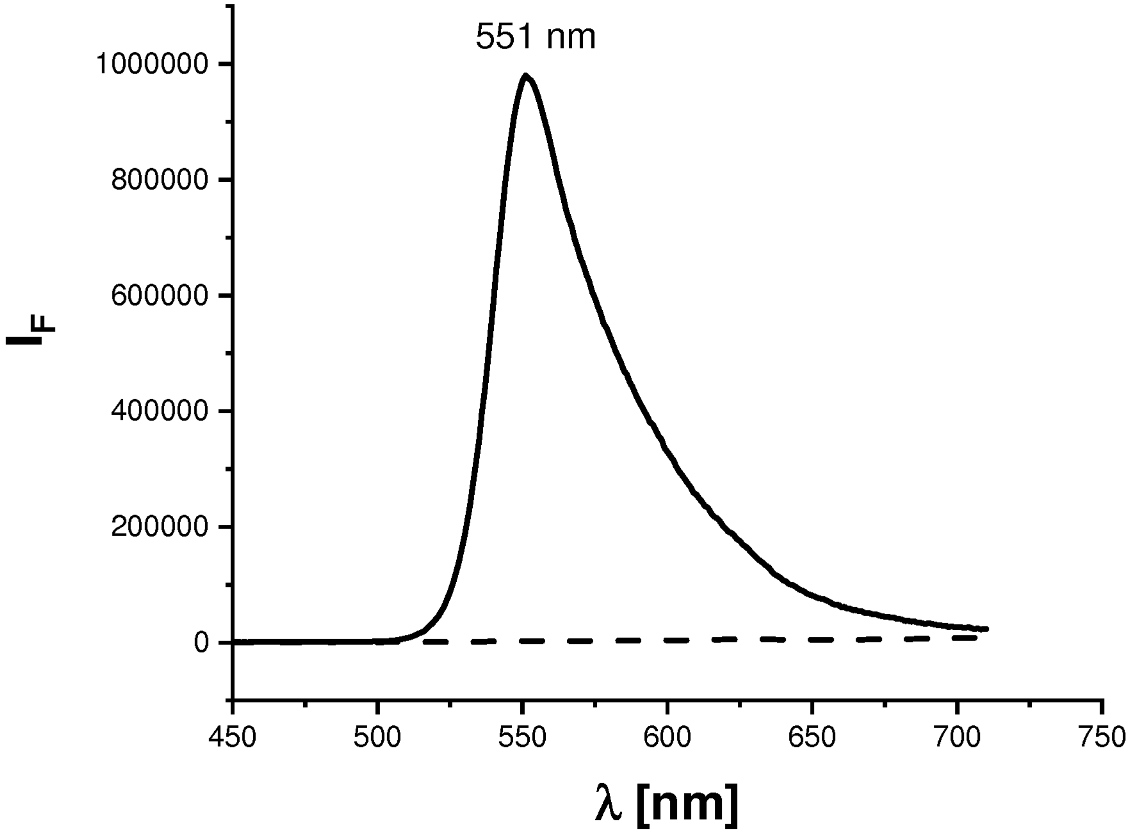
FIG. 8 shows the fluorescence spectra of compound (14'), before and after the reaction with the NOx-compound tert-butylnitrite at an excitation wavelength of 365 nm in toluene.
Figure 9:
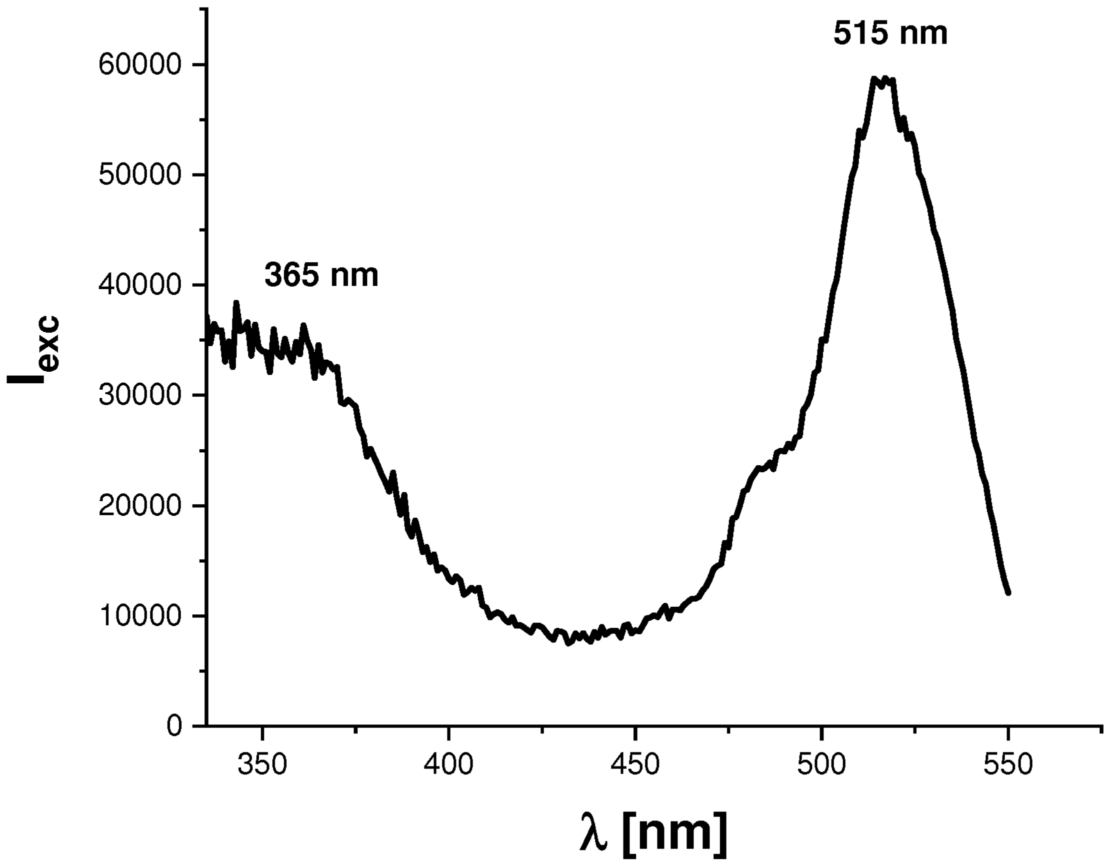
FIG. 9 shows the excitation spectra of compound (14') in toluene after reaction with the NOx-compound TBN.
Figure 10:
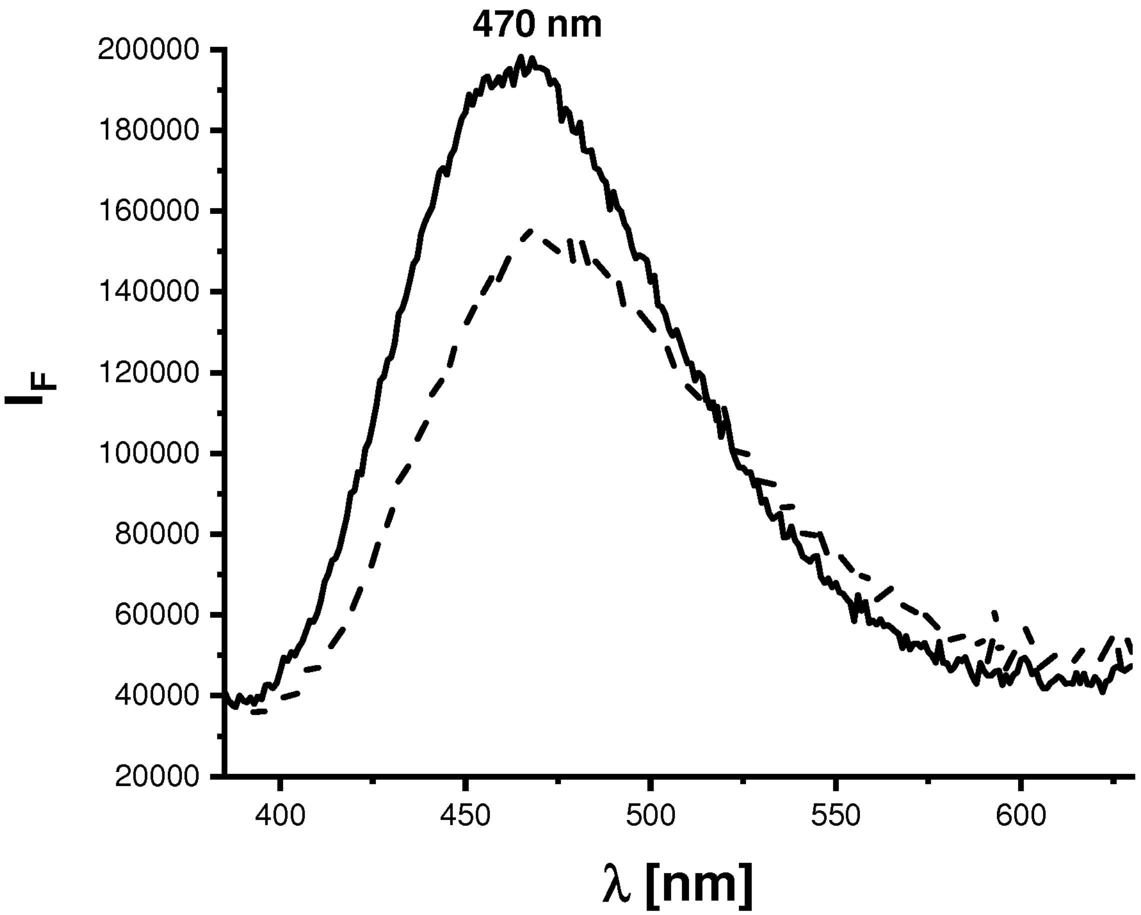
FIG. 10 shows the fluorescence spectra of compound (8') in HD1 (drop coated on a glass chip) before and after reaction with HNO3.
Figure 11:
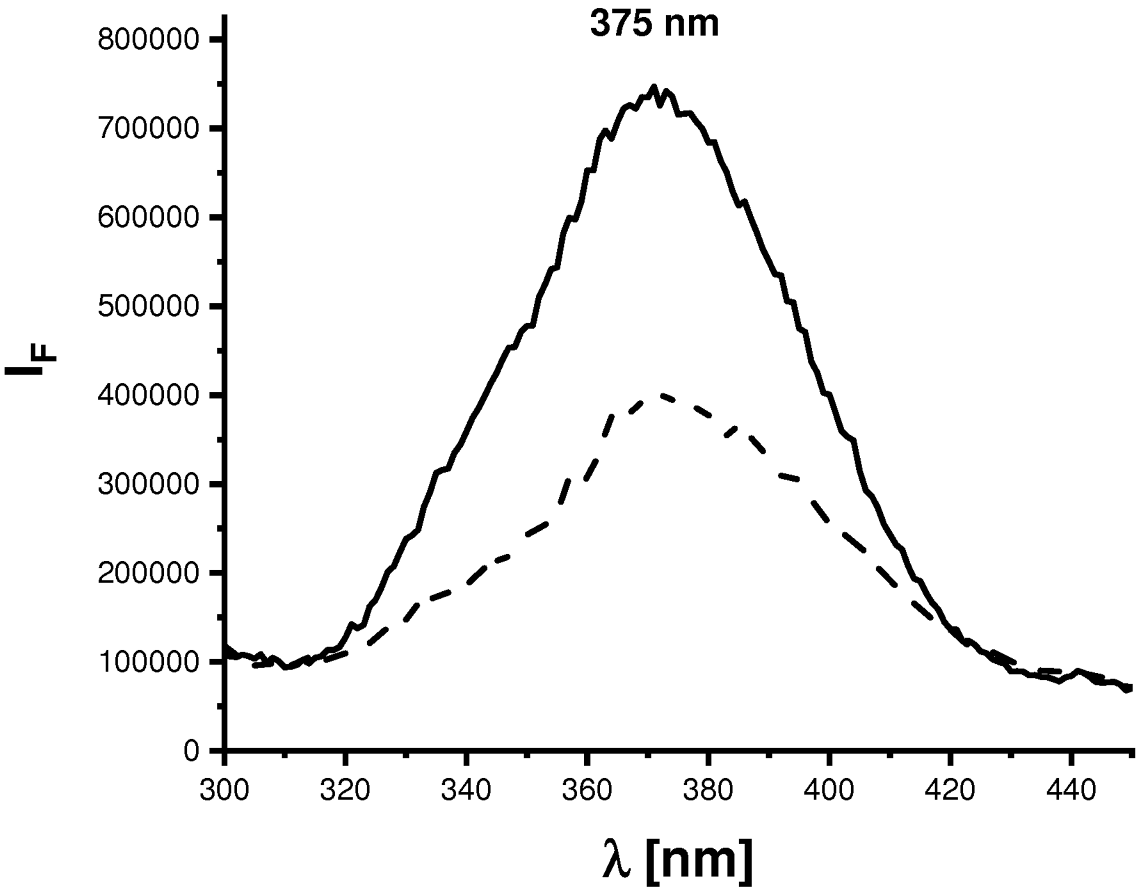
FIG. 11 shows the excitation spectra of compound (8') in HD1 (drop coated on a glass chip) before and after reaction with HNO3.
Figure 12:
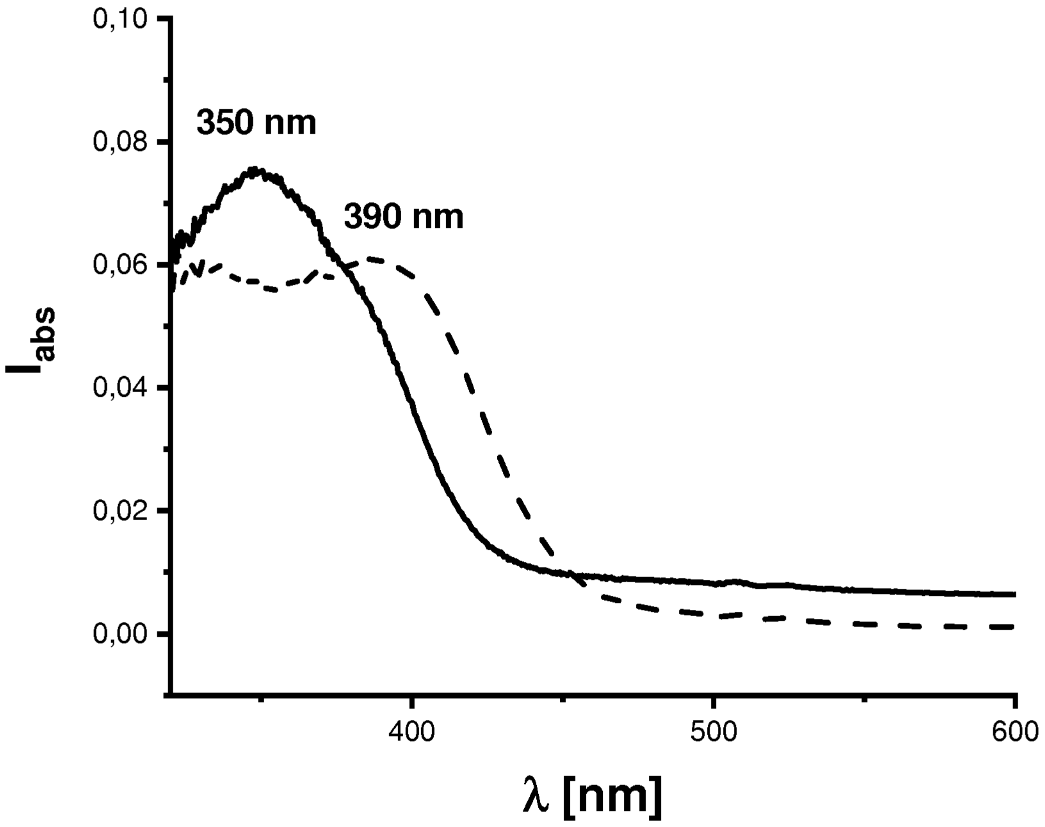
FIG. 12 shows the absorption spectra of compound (8') in HD1 (drop coated on a glass chip).
Figure 13:
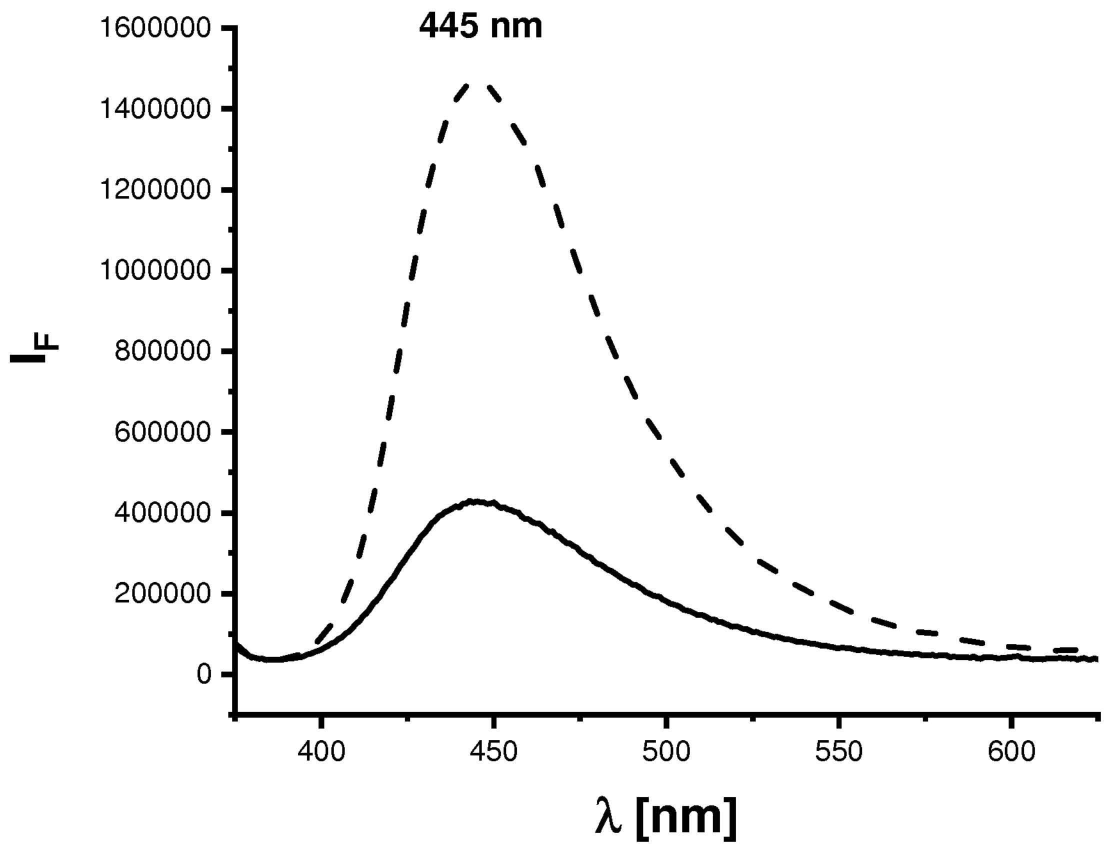
FIG. 13 shows the fluorescence spectra of compound (8') in polystyrene (drop coated on a glass chip), where a fluorescence decrease at 445 nm wavelength can be observed after reaction with HNO3.
Figure 14:
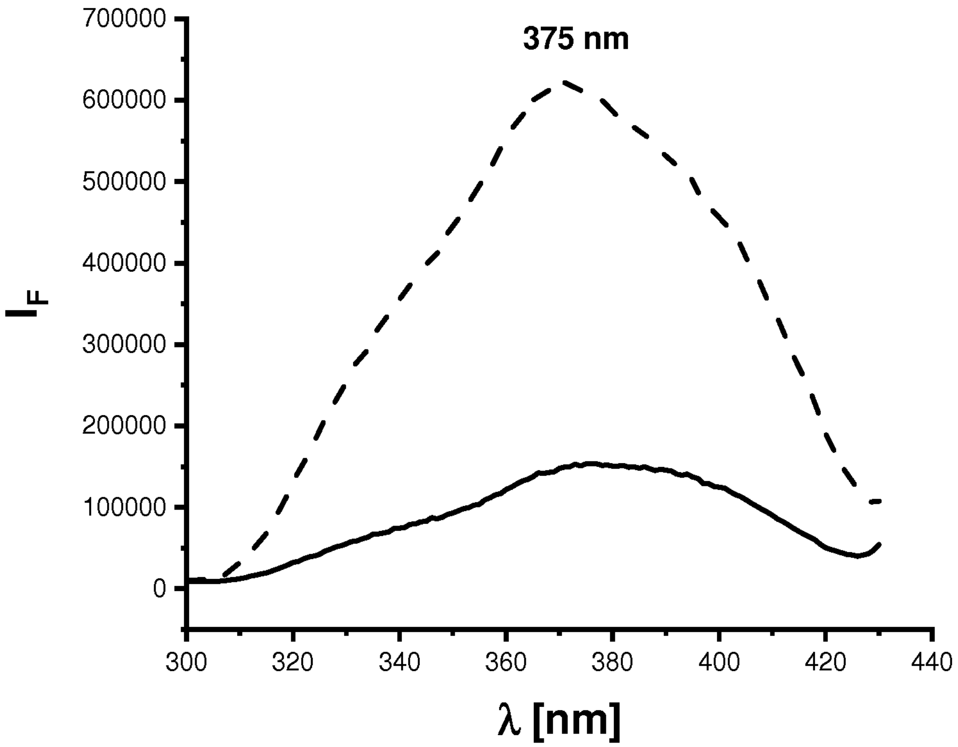
FIG. 14 shows the excitation spectra of compound (8') in polystyrene (drop coated on a glass chip).
Figure 15:
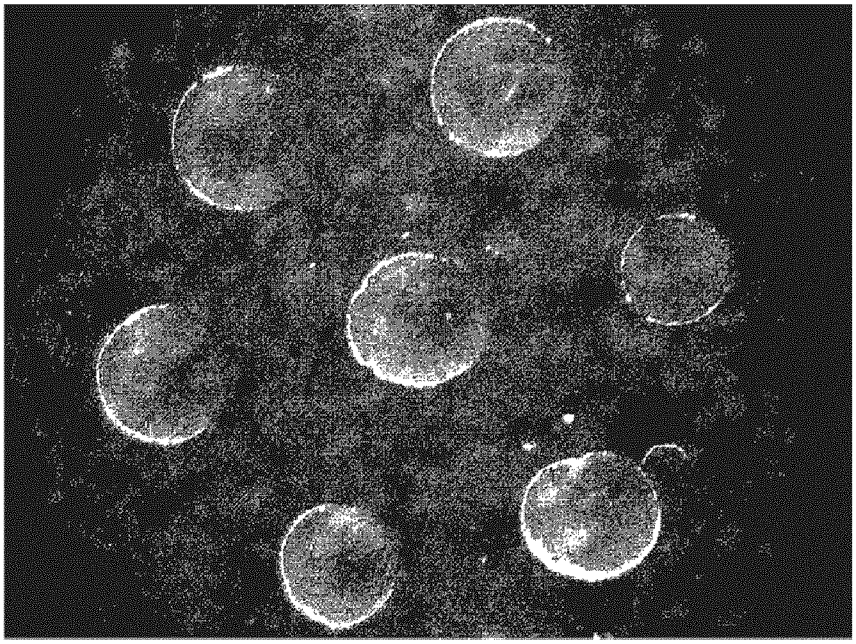
FIG. 15 shows a microscope image of 7 spots which have been spotted as described in Example 6 on a borosilicate glass surface (microscope cover plate).
Figure 16:
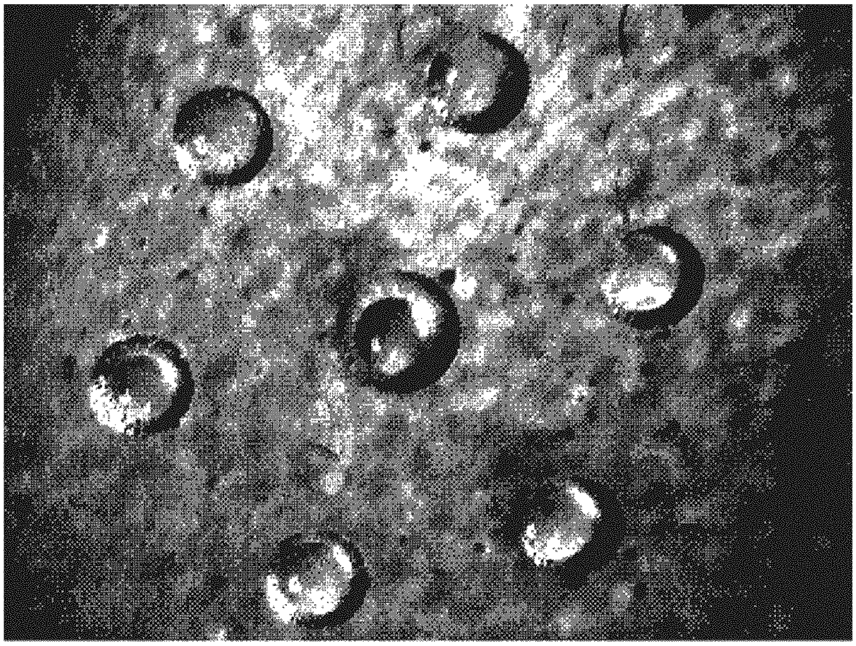
FIG. 16 shows a microscope image of 7 cavities in a cycloolefin copolymer 6013 (COC6013/(Topas Advanced Polymers), which have a concave spherical surface with a radius of 1 mm and a depth of 0.4 mm into which spots of a model mixture as described in Example 1, respectively Example 6 have been dispensed.

A Nafion coated Nomex foil was wiped over a glass area of 1 $cm^2$, that was coated with 1 μg $NH_4NO_3$ and was measured. A strong increase in fluorescence could be detected. The same measurement was repeated, leading to an even higher increase. FIG. 4 shows the fluorescence intensity of the sensor of example 3 (the catalyst Nafion is drop-coated in the channel right before the sensor layer). FIG. 5 shows the fluorescence intensity of the sensor of example 4 (the catalyst Nafion is drop-coated on a Teflon foil). First, the Nafion coated Teflon foil was measured, showing no change in fluorescence. Adding 2 μL of methanol on a Nafion coated Teflon foil, the measurement shows a slight decrease in fluorescence. 250 ng $NH_4NO_3$ show a strong increase in fluorescence. This measurement was repeated three times in total and an increase in fluorescence could always be observed. FIG. 6 shows the fluorescence intensity of the sensor layer of example 5 (the catalyst Nafion is drop-coated on a Teflon foil). First, 250 ng $NH_4NO_3$ were measured. An increase in fluorescence could be observed. This measurement was repeated, leading to another increase in fluorescence. Afterwards, 100 ng $NH_4NO_3$ were measured, showing a slight increase in fluorescence. 1 μg $NH_4Cl$ was measured, also showing an increase in fluorescence. 2 μg $NH_4Cl$ were measured, showing again an increase in fluorescence. Last, 250 ng $NH_4NO_3$ were measured, showing a slight increase in fluorescence. FIG. 7 shows the fluorescence spectra of a BODIPY™ dye according to formula (14) with $R^0$=Cl; further termed compound (14') before and after reaction with tert-butylnitrite (TBN) as $NO_x$ source at an excitation wavelength of 510 nm in toluene (example 7). A drastic increase at 551 nm can be observed. FIG. 8 shows the fluorescence spectra of compound (14'), before and after the reaction with the NOx-compound tert-butylnitrite at an excitation wavelength of 365 nm in toluene. Again, a strong increase in fluorescence at 551 nm can be observed. FIG. 9 shows the excitation spectra of compound (14') in toluene after reaction with the $NO_x$-compound TBN. An excitation band at 365 nm and a stronger one at 515 nm can be observed. FIG. 10 shows the fluorescence spectra of compound (8') in HD1 (drop coated on a glass chip) before and after reaction with $HNO_3$. An increase in fluorescence at 470 nm wavelength can be detected after reaction with $HNO_3$. FIG. 11 shows the excitation spectra of compound (8') in HD1 (drop coated on a glass chip) before and after reaction with $HNO_3$. An increase in the excitation intensity at 375 nm can be detected. FIG. 12 shows the absorption spectra of compound (8') in HD1 (drop coated on a glass chip). After reaction with $HNO_3$ the absorption maximum is shifted from 390 nm to 350 nm. FIG. 13 shows the fluorescence spectra of compound (8') in polystyrene (drop coated on a glass chip), where a fluorescence decrease at 445 nm wavelength can be observed after reaction with $HNO_3$. FIG. 14 shows the excitation spectra of compound (8') in polystyrene (drop coated on a glass chip). After reaction with $NO_x$, a decrease in the intensity at 375 nm is detected. FIG. 15 shows a microscope image of 7 spots which have been spotted as described in Example 6 on a borosilicate glass surface (microscope cover plate). FIG. 16 shows a microscope image of 7 cavities in a cycloolefin copolymer 6013 (COC6013/(Topas Advanced Polymers), which have a concave spherical surface with a radius of 1 mm and a depth of 0.4 mm into which spots of a model mixture as described in Example 1, respectively Example 6 have been dispensed.

The technical object of the described embodiments is to provide necessary elements of a device, the device itself, and its use, i.e. a method of analysis, for detecting minute amounts of nitrate explosives and products of their decomposition wherever they may occur: from soil samples, from wipe samples and from fluid extracts of different matrices. Therein, the detection is accomplished in fluid streams comprising gaseous or vaporized residues of the nitrate explosives. The method and device allow discriminating between residues of chlorides and nitrate explosives such as ammonium nitrate, ANFO (ammonium nitrate fuel oil) and urea nitrate. Accordingly, the device and method allow detection of these substances in nano- and picogram quantities.

Accordingly,

1. The analyte sensitive layer without the acidic catalyst allows the detection of nitrates by thermal decomposition of the nitrate to the decomposition products.

2. The analyte sensitive layer with the acidic catalyst placed on the swipe sample material or on the swipe sample heater, in/on the heated mouth or in the sensor chip allows the detection of nitrates by (thermal and) acidic decomposition of the nitrate to the decomposition products.

With respect to sensitivity the layer triarylborane dye (8) and the carrier material hydrogel HD1 described under example 4 was the best one.

With respect to selectivity the layer BODIPY™ dye (14) and the carrier material polystyrene described under point example 7 was the best one.

After the reaction with nitrates respectively with their decomposition products the fluorescence exhibits a strong increase in fluorescence intensity at wavelength between 440-560 nm.

Initially, hydrogel solutions were prepared of the selected triarylborane dye (3.76 mM) or the selected BODIPY™ dye (0.11 M) and applied to the substrate by spin coating or by drop coating to produce the layers. An acid e.g. Nafion or 4-bromobenzenesulfonic acid or a hydrogel/acid mixture or TBA salt/acid mixture or hydrogel/acid/TBA salt mixture or porous silica/acid/TBA salt mixture was used as the acid catalyst on the catalyst layer. Nafion, Hyflon, Aquivion, and 3M™ ionomer can also be used as swab/wipe materials or a wipe sample (swab sample) heater surface to decompose nitrates before they are carried by a (heated) gas stream to the fluorescence indicator.

EXAMPLES

In the examples given below, fluorescence measurements were made either using a FluoroMax spectrofluorimeter (HORIBA Jobin Yvon GmbH, Bensheim, Germany) or a prototype measurement set-up, configured similarly, and comprising a light source (LED emitting at 365 nm), a measurement chamber, and a sensitive photoelement comprising a photomultiplier. Sensitive layers were applied as layers of a thickness <1 mm in sample wells of a diameter of about 1 mm which were fluidically connected with channels of a microfluidic system. A fluid stream (e.g. air) containing the analyte was directed onto the surface of the layer(s) in the well(s).

Example 1

A sensor layer was prepared on a glass substrate by using the ether-based hydrophilic polyurethane Hydromed™-D1 and the triarylborane dye according to formula (8) with R═Me; in the following termed (8').

1. 379.8 mg HD1 were dissolved in 4231.3 mg EtOH and 519 mg $H_2O$ (solution A).
2. 2.0 mg of compound (8') were dissolved in 1.0 mL EtOH (solution B).
3. A mixture of 10 μL of solution A and 2 μL of solution B were put for 10 min at 30° C. in an ultrasonic bath.
4. 0.5 μL of the resulting mixture were applied onto the chosen substrate by drop-coating.

1 μL of analyte solution (1 mg $NH_4NO_3$/10 mL methanol) were placed on a Teflon foil. The methanol was evaporated over a period of 2 min and the Teflon foil was heated for 30 s and the signal measured. 2 μL Nafion (5% in a mixture of lower aliphatic alcohols and water), acting as catalyst for the decomposition of ammonium nitrate, were added to the channel right before the sensor layer, to achieve highest sensitivity. (FIG. 1)

1.0 mg $NH_4NO_3$ were dissolved in 10 mL methanol. 1 μL samples of this solution were placed on a Teflon foil. The methanol was evaporated over a period of 2 min and the Teflon foil was heated for 30 s and the signal measured. (FIG. 2)

Example 2

A sensor layer was prepared on a glass substrate by using the ether-based hydrophilic polyurethane Hydromed™-D1 and compound (8'):

1. 379.8 mg HD1 were dissolved in 4231.3 mg EtOH and 519 mg $H_2O$ (solution A).
2. 2.0 mg of compound (8') were dissolved in 1.0 mL EtOH (solution B).
3. A mixture of 10 μL of solution A and 2 μL of solution B were put for 10 min at 30° C. in an ultrasonic bath.
4. 0.5 μL of the resulting mixture were applied onto the chosen substrate by drop-coating.

1 μL of the analyte solution (1 mg $NH_4NO_3$/10 mL methanol) were placed on a Nomex foil, coated with 3 μL Nafion (5% in a mixture of lower aliphatic alcohols and water). The Nomex foil then was instantly heated for 30 s and the signal measured. (FIG. 3)

Example 3

A sensor layer was prepared on a glass substrate by using polystyrene and compound (8'):

1. 59 mg polystyrene were dissolved in 700 μL $CHCl_3$ (solution C).
2. 2.0 mg of compound (8') were dissolved in 1.0 mL EtOH (solution B).
3. A mixture of 10 μL of solution C and 2 μL of solution B were put for 10 min at 30° C. in an ultrasonic bath.
4. 0.5 μL of the resulting mixture were applied onto the chosen substrate by drop-coating.

1 μL of the analyte solution (1 mg $NH_4NO_3$/10 mL methanol were placed on a Teflon foil. The methanol was evaporated over a period of 2 min, the Teflon foil was heated for 30 s and the signal measured. 2 μL Nafion (5% in a mixture of lower aliphatic alcohols and water), acting as catalyst for the decomposition of $NH_4NO_3$, were added to the channel right before the sensor layer, to achieve highest sensitivity. (FIG. 4)

Example 4

A sensor layer was on a glass substrate by using the ether-based hydrophilic polyurethane Hydromed™-D1 and compound (8'):

1. 2155 mg solution A were dissolved in 3168 mg EtOH and 660 mg $H_2O$ (solution D).
2. 2.0 mg of compound (8') were dissolved in 1.0 mL EtOH (solution B).
3. A mixture of 10 μL of solution D and 2 μL of solution B were put for 10 min at 30° C. in an ultrasonic bath.
4. 0.5 μL of the resulting mixture were applied onto the chosen substrate by drop-coating.

1 μL of the analyte solution (1 mg $NH_4NO_3$/10 mL methanol) were placed on a Teflon foil, coated with 3 μL Nafion (5% in a mixture of lower aliphatic alcohols and water). The Teflon foil then was instantly heated for 30 s and the signal measured. (FIG. 5)

Example 5

A sensor layer was on a glass substrate by using the ether-based hydrophilic polyurethane Hydromed™-D1 and a triarylborane dye according to formula (7), whereas $R_9$-$R_{16}$=H and $R_1$=CO—$NHNH_2$, in the following termed (7'):

1. 2155 mg solution A were dissolved in 3168 mg EtOH and 660 mg $H_2O$ (solution D).
2. 2.0 mg of compound (7') were dissolved in 1.0 mL EtOH (solution E).
3. A mixture of 10 μL of solution D and 2 μL of solution E were put for 10 min at 30° C. in an ultrasonic bath.
4. 0.5 μL of the resulting mixture were applied onto the chosen substrate by drop-coating.

Example 6

Model indicator layers were prepared as described below. The aim of the experiment was the contactless needle dosing of an exemplary prepared mixture, according to the composition obtained according to Example 1 (see above). The medium has been dispensed in point form into cavities of a model substrate. The suspension is to be metered precisely and without contamination of the environment and contactlessly. A high repeat accuracy in quantity and positioning can be achieved. Volumes of 0.1-1 μL were applied repeatedly as described in more detail below (cf. FIGS. 15 and 16).

The sample was reproducibly dispensed with a PIEZO ACTUATOR PICO PULSE HD and FLUID ASSY PULSE 5.0 S D30 (Nordson EFD, nordsonefd.com) in combination with a 200 μm needle. The dosing quantity has been adjusted by the parameters dosing time, delivery pressure and number of dosing cycles. Sequential points were processed with a feed rate of 20 mm/sec. The dosing process was very stable with the dosing parameters listed below. The medium was remixed after 5-10 minutes to avoid any possible segregation of the components. Shortly before dosing, the needle was rinsed and pulsed briefly with a high frequency. Dosing was carried out without downtimes. After a standstill or pause times, impurities/residues at the needle outlet opening, must be removed for example with aqueous ethanol. The experimental parameters used are: dosing time: 0.30 ms; cycle time: 10.00 ms; dosing pulses: 4; opening edge: 0.25 ms; closing edge: 0.20 ms; stroke: 80(%); volt close: 110 V; temperature: 21° C. (room temperature); delivery pressure medium: 1.0 bar; feed rate: 20 mm/sec; dosing distance: 0.05-0.6 mm, e.g., 0.1-0.5 mm, particularly 0.1-0.3 mm, depending on dosing quantity; dosing weight: 1.09 mg for these parameters (7 cavities).

Example 7

1 μL of the 0.11 M solution BODIPY™ dye according to formula (14), where $R_0$ =Cl, in 2.5 mL toluene and 1 μL tert-butylnitrite (0.11 M in toluene) are added in a cuvette.

1 μL of the analyte solution (1 mg $NH_4NO_3$/10 mL methanol) were placed on a Teflon foil, coated with 3 μL Nafion (5% in a mixture of lower aliphatic alcohols and water). The Teflon foil then was instantly heated for 30 s and the signal measured. (FIG. 6)

Corresponding graphs of the observed fluorescence intensity are shown in FIGS. 1 through 6 (corresponding to examples 1-5) and absorption, fluorescence emission and excitation spectra of the fluorescent dyes (corresponding to compounds (8) and (14), where $R^0$ =Cl) shown in FIGS. 7 through 14.

The present invention has been explained with reference to various illustrative embodiments and examples. These embodiments and examples are not intended to restrict the scope of the invention, which is defined by the claims and their equivalents. As is apparent to one skilled in the art, the embodiments described herein can be implemented in various ways without departing from the scope of what is invented. Various features, aspects, and functions described in the embodiments can be combined with other embodiments.

The invention claimed is:

1. A molecular probe, wherein the molecular probe is configured for selective detection of a nitrate and/or a decomposition product of a nitrate by generating a fluorescence signal in response to an excitation at 365 nm, wherein the molecular probe is a triarylborane dye according to formula (7):

(7)

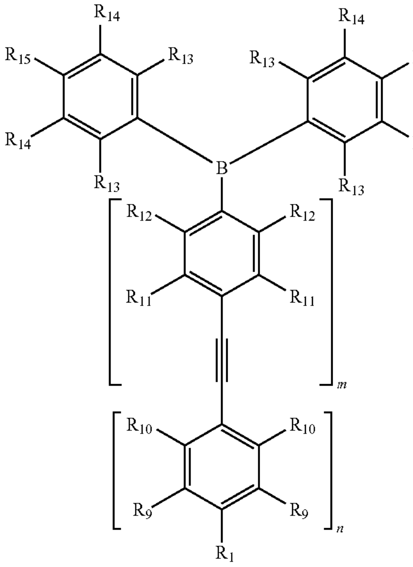

wherein $R_1$ is selected from the group consisting of $NHCH_2CH_2NH_2$, $NHCH_2CH_2NH$(alkyl), $NHCH_2CH_2NHPh$, $NHCH_2CH_2NHAr$, $NHNH_2$, NHNHMe, NHNHPh, NHNHAr, $NHNHCH_2CH_2NH_2$, $NHNHCH_2CH_2NH$(alkyl), $NHNHCH_2CH_2NHPh$, $NHNHCH_2CH_2NHAr$, CO—$NHCH_2CH_2NH_2$, CO—$NHNH_2$, CO—NHNHMe, CO—$NHNHCH_2CH_2NH_2$, CO—$NHNHCH_2CH_2NHPh$, CO—$NHNHCH_2CH_2NHAr$, NH—CO—$NHNH_2$, NHNH—CO—$NHNH_2$, NHNH—CO—$NH_2$, NH—CS—NHNH—CO—Me, NH—CO—NHNH—CO—Me, CO—NHNH—CS—$NH_2$, NH—CS—NHNH—CO-alkyl, CO—NHNH—CS—NH(alkyl), (a)

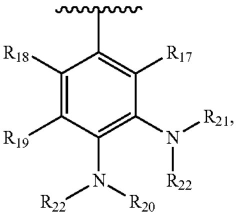

(b)

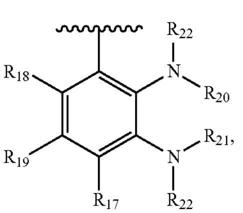

(c)

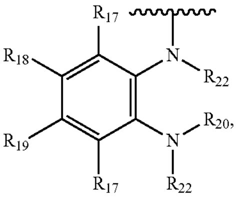

-continued (d)

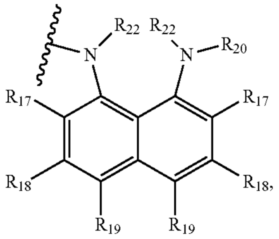

and regioisomers of the amine groups of (a)-(d);

$R_{17}$ is selected from the group consisting of H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N$(alkyl)$_2$, OH, OMe, OiPr, and O(alkyl);

$R_{18}$ is selected from the group consisting of H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N$(alkyl)$_2$, OH, OMe, OiPr, and O(alkyl);

$R_{19}$ is selected from the group consisting of H, Me, alkyl, phenyl, benzyl, aryl, F, Cl, Br, I, $CF_3$, $NH_2$, $NO_2$, $CO_2H$, $CH_2OH$, $CH_2O$(alkyl), $CH_2NMe_2$, $CH_2N$(alkyl)$_2$, OH, OMe, OiPr, and O(alkyl);

$R_{20}$ is selected from the group consisting of H, Me, Et, alkyl, phenyl, benzyl, aryl, $CF_3$, CO—Me, CO-alkyl, CO-aryl, $NH_2$, OMe, OiPr, and O(alkyl);

$R_{21}$ is selected from the group consisting of H, Me, Et, alkyl, phenyl, benzyl, aryl, $CF_3$, CO—Me, CO-alkyl, CO-aryl, $NH_2$, OMe, OiPr, and O(alkyl);

$R_{22}$ is H, each of $R_9$, $R_{10}$, $R_{11}$, $R_{12}$, $R_{13}$, and $R_{14}$ is independently selected from the group consisting of H, Me, alkyl, phenyl, benzyl, aryl, F, Cl, Br, I, —$CF_3$, —$CH_2OH$, —$CH_2O$alkyl, —$CH_2NMe_2$, —$CH_2N$(alkyl)$_2$, —$CH_2P$(tBu)$_2$, —$CH_2P$(alkyl)$_2$, —OMe, —OiPr, —O(alkyl), —$NH_2$, —NHMe, —NH(alkyl), —$NEt_2$, —N(alkyl)$_2$, —NHPh, —NHAr, —$NHNH_2$, —NHNHMe, —$NHNMe_2$, —$NHNEt_2$, —NHN(alkyl)$_2$, —NHNHPh, —NHNHAr, —$NHNPh_2$, —$NHNAr_2$, —CO—$NH_2$, —CO—NHMe, —CO—$NMe_2$, —CO—$NEt_2$, —CO—N(alkyl)$_2$, —CO—NHPh, —CO—NHAr, —CO—$NHNH_2$, —CO—NHNHMe, —CO—$NHNMe_2$, —CO—$NHNEt_2$, and —CO—NHN(alkyl)$_2$, and i) each of $R_{15}$, and $R_{16}$ is independently selected from the group consisting of H, Me, alkyl, phenyl, benzyl, aryl, F, Cl, Br, I, —$CF_3$, —$CH_2OH$, —$CH_2O$(alkyl), —$CH_2NMe_2$, —$CH_2N$(alkyl)$_2$, —$CH_2P$(tBu)$_2$, —$CH_2P$(alkyl)$_2$, —OMe, —OiPr, —O(alkyl), —$NH_2$, —NHMe, —NH(alkyl), —$NEt_2$, —N(alkyl)$_2$, —NHPh, —NHAr, —$NHNH_2$, —NHNHMe, —$NHNMe_2$, —$NHNEt_2$, —NHN(alkyl)$_2$, —NHNHPh, —NHNHAr, —$NHNPh_2$, —$NHNAr_2$, —CO—$NH_2$, —CO—NHMe, —CO—$NMe_2$, —CO—$NEt_2$, —CO—N(alkyl)$_2$, —CO—NHPh, —CO—NHAr, —CO—$NHNH_2$, —CO—NHNHMe, —CO—$NHNMe_2$, —CO—$NHNEt_2$, and —CO—NHN(alkyl)$_2$, or ii) each of $R_{15}$, and $R_{16}$ is selected from the group consisting of H, F, Cl, Br, I, Me, alkyl, phenyl, aryl, vinyl, alkynyl, $CF_3$, $NMe_2$, $NPh_2$, and $BMes_2$; or iii) each of $R_{15}$ and $R_{16}$ is independently selected from the group consisting of

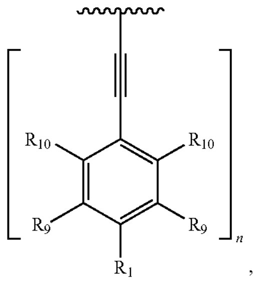

with n and m being independently selected from the group consisting of 0, 1, 2, 3, and 4; wherein n+m≥1.

2. The molecular probe according to claim 1, wherein each of $R_9$, $R_{10}$, $R_{11}$, $R_{12}$, and $R_{14}$ is H, and the triarylborane dye according to formula (7) is a triarylborane dye according to formula (6):

(6)

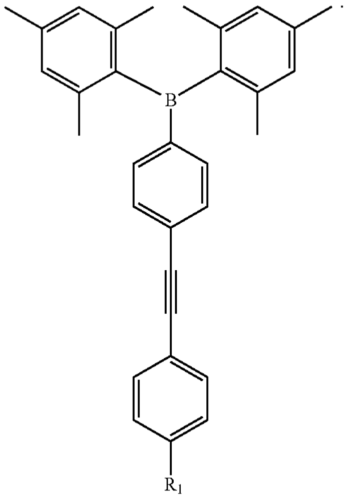

3. The molecular probe according to claim 1, wherein the triarylborane dye is selected from the group consisting of a substance according to formula (8), (9), and (10):

(8)

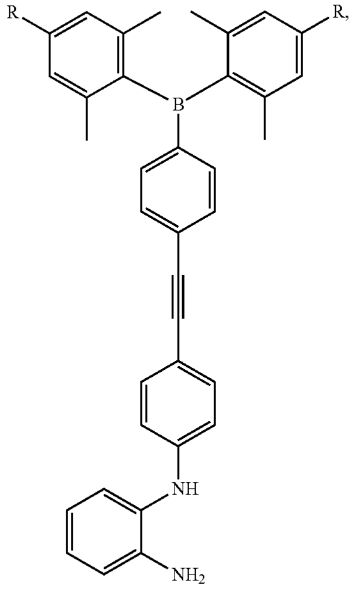

(9)

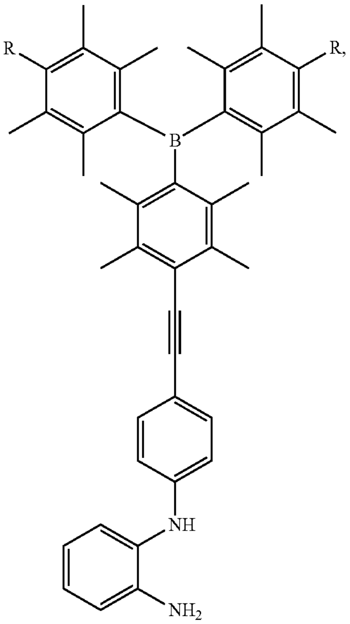

-continued (10)

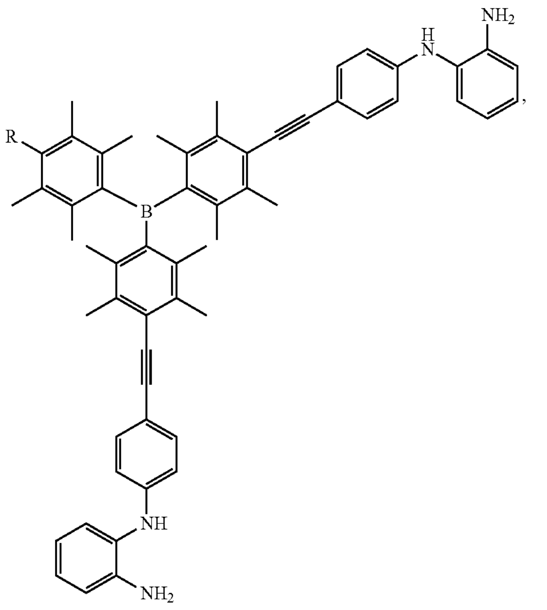

wherein

R is selected from the group consisting of H, F, Cl, Br, I, Me, alkyl, phenyl, aryl, vinyl, alkynyl, $CF_3$, $NMe_2$, $NPh_2$, and $B(Mes)_2$.

4. The molecular probe according to claim 1, wherein the triarylborane dye is selected from the group consisting of a substance according to formula (11):

(11)

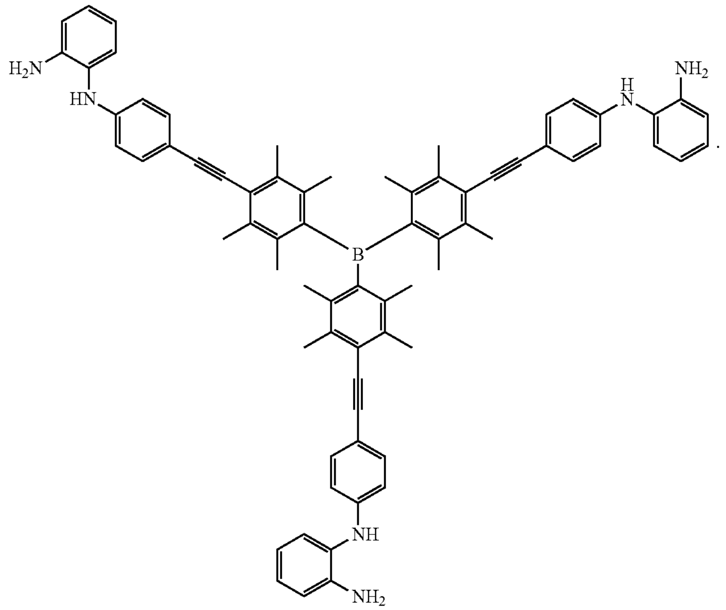

5. A fluorescent indicator, wherein the fluorescence indicator is configured for detection of an explosive based on a nitrate and/or for detection of a decomposition product of a nitrate by generating a fluorescence signal in response to an excitation at 365 nm, comprising the following constituents:

a molecular probe according to claim 1, a carrier material, and a substrate;

wherein the molecular probe and the carrier material are homogeneously distributed within an indicator layer which is deposited on the substrate.

6. The fluorescence indicator according to claim 5, wherein the indicator layer comprises a sulfonic acid or a salt thereof, wherein the sulfonic acid or salt thereof is selected from the group consisting of a substance according to formula (1), (2), (3), (4) and (5):

(1)

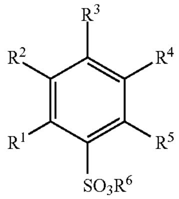

(2)

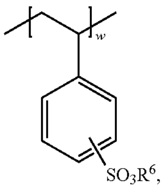

-continued (3)

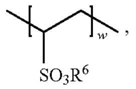

(4)

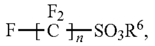

(5)

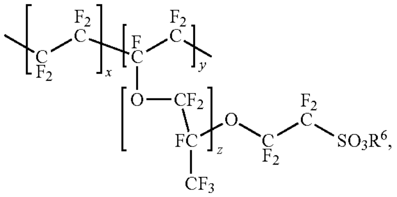

wherein each of $R_1$, $R_2$, $R_3$, $R_4$, and $R_5$ is independently from each other selected from the group consisting of H, Me, Et, Pr, alkyl, vinyl, phenyl, aryl, benzyl, F, Cl, Br, I, $CF_3$, $CH_2OH$, $CO_2H$, $PO_3H_2$, OH, OMe, O(alkyl), O(aryl), CN, $NO_2$, $NH_2$, $SO_3H$, and $SO_3$;

and $R_6$ is selected from the group consisting of H, Na, K, Ag, tetrabutylammonium, tetraoctylammonium, and tetraalkylammonium;

w=8-500, q≥8, x=y=50-150, and z=0, 1, 2, or 3.

7. The fluorescence indicator according to claim 6, wherein the sulfonic acid or the salt thereof is selected from the group consisting of a perfluorosulfonic acid or a salt thereof according to formula (4) and (5).

8. The fluorescence indicator according to claim 6, wherein the sulfonic acid or the salt thereof is a substance according to formula (1).

9. The fluorescence indicator according to claim 8, wherein each of $R_1$, $R_2$, $R_3$, $R_4$ and $R^5$ is independently selected from the group consisting of H and I.

10. The fluorescence indicator according to claim 5, wherein the carrier material is selected from the group consisting of a polymer, an amphiphilic macromolecule, and a porous silica material, wherein the polymer is dissolved in a mixture of an organic solvent with water or in a pure organic solvent, wherein the polymer is selected from the group consisting of:

a polyurethane/polyether-based hydrogel;

a block copolymer, and a polystyrene, or wherein the polymer is selected from the group consisting of a hydrophilic polyurethane, an aliphatic polyether-based polyurethane, and the block copolymer, wherein the hydrophilic polyurethane is an ether-based hydrophilic polyurethanes, wherein the block copolymer is selected from the group consisting of a hydrophilic block linked with a polystyrene, and a nonionic triblock copolymers composed of poly(propylene oxide) and poly(ethylene oxide) units.

11. The fluorescence indicator according to claim 10, wherein the porous silica material is a fumed silica.

12. The fluorescence indicator according to claim 5, wherein the carrier material comprises a polymer and wherein the polymer is selected from the group of polymers consisting of a poly(ethylene glycol) having a molecular weight of $M_n$=35,000, 20,000, 12,000, or 10,000;

a poly(ethylene glycol) methyl ether having a molecular weight of $M_n$=35,000, 20,000, 12,000, or 10,000, a poly(ethylene glycol) dimethyl ether having a molecular weight of $M_n$=35,000, 20,000, 12,000, or 10,000, a poly(ethylene glycol) dialkyl ether having a molecular weight of $M_n$=35,000, 20,000, 12,000, or 10,000, a poly(ethylene glycol) diacrylate having a molecular weight of $M_n$=35,000, 20,000, 12,000, 10,000, or 6,000, a poly(ethylene glycol) dimethacrylate having a molecular weight of $M_n$=35,000, 20,000, 12,000, 10,000, or 6,000, a polyvinyl alcohol, a polyvinyl pyrrolidone, a poly(diallyldimethylammonium chloride) and a co-polymer comprising at least one of the polymers.

13. A method of fabricating an indicator layer, the indicator layer being adapted for fluorescence detection of an explosive based on a nitrate and/or for detection of a decomposition product of a nitrate-based explosive in response to an excitation at 365 nm, the method comprising:

mixing the triarylborane dye according to claim 1 with a carrier material, wherein the carrier material is selected from the group consisting of a polymer, an amphiphilic macromolecule, and a porous silica material, wherein the polymer is dissolved in a mixture of an organic solvent with water or in a pure organic solvent, wherein the polymer is selected from the group consisting of a polyurethane/polyether-based hydrogel;

a block copolymer, and a polystyrene, or wherein the polymer is selected from the group consisting of a hydrophilic polyurethane, an aliphatic polyether-based polyurethane, and the block copolymer, wherein the hydrophilic polyurethane is an ether-based hydrophilic polyurethane, wherein the block copolymer is selected from the group consisting of a hydrophilic block linked with a polystyrene, and a nonionic triblock copolymer composed of poly(propylene oxide) and poly(ethylene oxide) units, and spotting the triarylborane dye mixed with the carrier material on a substrate, which is stable up to a temperature of at least 100° C., wherein the spotting is being carried out using a nozzle, the nozzle being adjusted at a distance of 0.05-2 mm from the substrate.

14. The method of fabricating the indicator layer according to claim 13, wherein the substrate is a constituent of a microfluidic system and is a cyclic olefin polymer (COP).

15. The method of fabricating the indicator layer according to claim 13, further comprising:

storing the indicator layer in an inert atmosphere.

16. A method for selective detection of an analyte selected from the group consisting of a nitrate, nitric acid, nitrous acid and a nitric oxide by measuring a fluorescence, the method comprising:

providing a fluorescence indicator for detection of an explosive based on a nitrate and/or for detection of a decomposition product of a nitrate by generating a fluorescence signal in response to an excitation at 365 nm, comprising the following constituents:

the molecular probe according to claim 1, a carrier material, and a substrate;

wherein the molecular probe and the carrier material are homogeneously distributed within an indicator layer which is deposited on the substrate;

providing the analyte, wherein the analyte is either gaseous or collected on a swab or wipe;

vaporizing the analyte using a heater when the analyte is collected on the swab or wipe;

directing on the indicator layer comprising the molecular probe a fluid stream comprising the gaseous or vaporized analyte;

exposing the indicator layer to an excitation light;

measuring a fluorescence intensity over a time interval of <10 s and detecting a fluorescence increase; and detecting the analytes qualitatively and/or quantitatively by using a calibration curve.

17. The method according to claim 16, wherein directing the fluid stream on the indicator layer comprises heating the indicator layer to 50-100° C., wherein the fluid stream is air having a temperature within a range from 15-200° C.

18. The method according to claim 17, wherein the nitrate, nitric acid, nitrous acid and/or nitric oxide is collected with a swab or wipe and the fluid stream is generated such as to stream from the swab or the wipe through a channel of a microfluidic system comprising the indicator layer, wherein the swab and the wipe comprise a perfluorosulfonic acid according to formula (4) or (5');

(4)

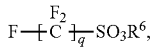

(5')

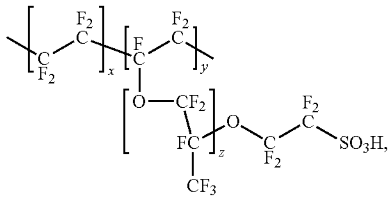

with q≥8, x=y=50-150, and z=0, 1, 2, or 3.

* * * * *